(12) United States Patent
Madsen et al.

(10) Patent No.: US 8,962,794 B2
(45) Date of Patent: Feb. 24, 2015

(54) INSULINS WITH AN ACYL MOIETY COMPRISING REPEATING UNITS OF ALKYLENE GLYCOL CONTAINING AMINO ACIDS

(75) Inventors: Peter Madsen, Bagsvaerd (DK); Thomas Boerglum Kjeldsen, Virum (DK); Janos Tibor Kodra, Koebenhavn OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 607 days.

(21) Appl. No.: 12/673,337

(22) PCT Filed: Aug. 15, 2008

(86) PCT No.: PCT/EP2008/060734
§ 371 (c)(1),
(2), (4) Date: Aug. 2, 2010

(87) PCT Pub. No.: WO2009/022006
PCT Pub. Date: Feb. 19, 2009

(65) Prior Publication Data
US 2011/0098439 A1      Apr. 28, 2011

Related U.S. Application Data

(60) Provisional application No. 60/956,399, filed on Aug. 17, 2007.

(30) Foreign Application Priority Data

Aug. 15, 2007  (EP) .................................. 07114387

(51) Int. Cl.
*C07K 14/62*   (2006.01)
*A61K 38/00*   (2006.01)

(52) U.S. Cl.
CPC   *C07K 14/62* (2013.01); *A61K 38/00* (2013.01)
USPC ........................................................ 530/303

(58) Field of Classification Search
None
See application file for complete search history.

(56) References Cited

U.S. PATENT DOCUMENTS

| 6,858,580 B2 | 2/2005 | Ekwuribe et al. |
| 6,869,930 B1 | 3/2005 | Havelund et al. |
| 2006/0183668 A1 | 8/2006 | Jonassen et al. |

FOREIGN PATENT DOCUMENTS

| EP | 2007/057321 | 2/2008 |
| WO | WO 99/22754 | 5/1999 |
| WO | 2005/012347 A2 | 2/2005 |
| WO | WO 2006/082205 | 8/2006 |
| WO | WO 2006082204 A1 * | 8/2006 |
| WO | 2007/096431 A1 | 8/2007 |

OTHER PUBLICATIONS

Clement, Stephen et al., "Oral insulin product hexyl-insulin monoconjugate 2 (HIM2) in type 1 diabetes mellitus: the glucose stabilization effects of the HIM2," Diabetes Technology & Therapeutics, 2002, vol. 4, No. 4, pp. 459-466.

Clement Stephen et al., "Oral modified insulin (HIM2) in patients with type 1 diabetes mellitus: results from a phase I/II clinical trial," Metabolism Clinical and Experimental, 2004, vol. 53, No. 1, pp. 54-58.

Walsh, Gary, "Therapeutic insulins and their large-scale manufacture," Applied Microbiology and Biotechnology, Springer-Verlag, BE, 2005, vol. 67, No. 2, pp. 151-159.

* cited by examiner

*Primary Examiner* — Robert A Wax
*Assistant Examiner* — Jessica Worsham
(74) *Attorney, Agent, or Firm* — Rosemarie R. Wilk-Orescan

(57) ABSTRACT

Acylated insulins wherein an acyl moiety is attached to the parent insulin and wherein said acyl moiety comprises repeating units of alkylene glycol containing amino acids and wherein there is only one lysine residue (K & Lys) in the parent insulin have satisfactory properties when administered pulmonary.

4 Claims, 1 Drawing Sheet

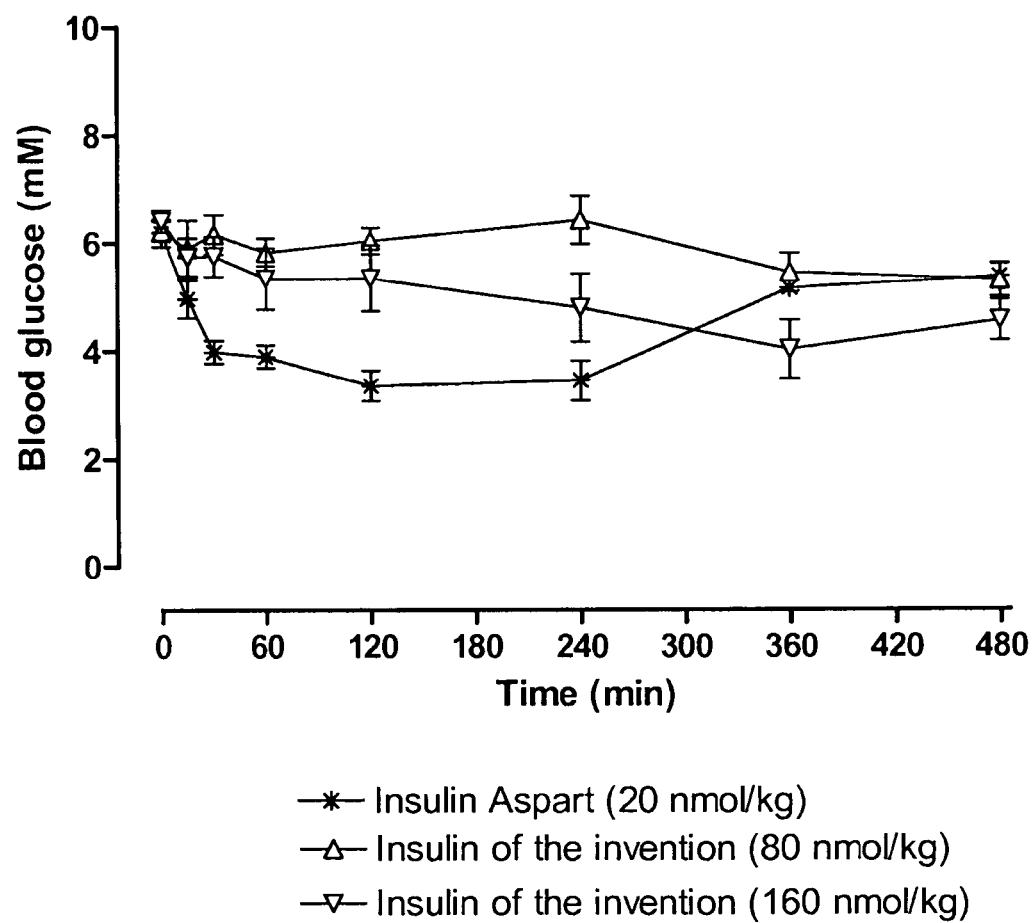

INSULINS WITH AN ACYL MOIETY COMPRISING REPEATING UNITS OF ALKYLENE GLYCOL CONTAINING AMINO ACIDS

CROSS-REFERENCE TO RELATED APPLICATIONS

This application is a 35 U.S.C. §371 national stage application of International Patent Application PCT/EP2008/060734 (published as WO 2009/022006), filed Aug. 15, 2008, which claimed priority of European Patent Application 07114387.9, filed Aug. 15, 2007; this application further claims priority under 35 U.S.C. §119 of U.S. Provisional Application 60/956,399, filed Aug. 17, 2007.

FIELD OF THIS INVENTION

The present invention relates to novel acylated insulin analogues and related aspects.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jan. 12, 2010. The Sequence Listing is made up of 2 kilobytes, and the information contained in the attached "SEQUENCE LISTING" is identical to the information in the specification as originally filed. No new matter is added.

BACKGROUND OF THIS INVENTION

Insulin is a polypeptide hormone secreted by β-cells of the pancreas. Insulin consists of two polypeptide chains designated the A and B chains which are linked together by two inter-chain disulphide bridges. In human, porcine and bovine insulin, the A and B chains contains 21 and 30 amino acid residues, respectively. However, from species to species, there are variations among the amino acid residues present in the different positions in the two chains. The widespread use of genetic engineering has made it possible to prepare analogues of natural occurring insulins by exchanging one of more of the amino acid residues.

Insulin is used for the treatment of diabetes and diseases connected therewith or resulting from it. Insulin is essential in maintaining normal metabolic regulation. Usually, insulin is administered by injections. Unfortunately, many diabetics are unwilling to undertake intensive therapy due to the discomfort associated with the many injections required to maintain close control of glucose levels. Upon oral administration, insulin is rapidly degraded in the gastro intestinal tract and is not absorbed into the blood stream. Therefore, alternate routes for administering insulin, such as oral, rectal, transdermal, and nasal routes have been investigated. Thus far, however, these routes of administration have not resulted in sufficiently effective insulin absorption.

For decades, both long-acting insulin preparations and fast acting insulin preparations have been available and many patients take 2-4 injections per day. In the last decades, it has turned out that it is extremely important for a diabetic patient to maintain close control of the blood glucose level.

Efficient pulmonary delivery of a protein is dependent on the ability to deliver the protein to the deep lung alveolar epithelium. Proteins that are deposited in the upper airway epithelium are not absorbed to a significant extent. This is due to the overlying mucus which acts as a barrier to absorption. In addition, proteins deposited on this epithelium are cleared by mucociliary transport up the airways and then eliminated via the gastrointestinal tract. The extent to which proteins are not absorbed and instead eliminated by these routes depends on their solubility, their size, as well as other less understood characteristics. The properties of peptides can be enhanced by grafting organic chain-like molecules onto them. Such grafting can improve pharmaceutical properties such as half life in serum, stability against proteolytical degradation and reduced immunogenicity.

International patent application number PCT/EP2007/057321 which will be published around 21 Jan. 2008 (our ref.: 7460) describes PEGylated insulins having no acyl groups. International patent application number PCT/EP2007/which will be published around 29 Aug. 2007 (our ref.: 7302) describes insulins having a complex side chain with no alkylene glycol moieties. International patent application having publication number WO 2006/082205 (our ref.: 7142) describes insulins having a complex side chain.

A vaguely defined human insulin product designated MIH2 is described in Diabetes Technology & Therapeutics 4 (2002), 459-66, and in Metabolism 53 (2004), 54-8. Similar and related products are described in U.S. Pat. No. 6,858,580. US patent application No. 2006/0183668 describes in claim 1 an insulin derivative which is a naturally occurring insulin or an analogue thereof which has side chain attached to the α-amino group of the N-terminal amino acid residue of the B chain or to the ε-amino group of a Lys residue present in the B chain of the parent insulin, the side chain being of the formula —W—X—Y—Z each of which re as defined therein.

DEFINITIONS

Herein, the term insulin covers natural occurring insulins, e.g., human insulin, as well as insulin analogues thereof.

Herein, the term insulin analogue covers a polypeptide which has a molecular structure which formally can be derived from the structure of a naturally occurring insulin, e.g., human insulin, by deleting and/or substituting (replacing) one or more amino acid residue occurring in the natural insulin. Preferably, the substituted amino acid residues are codable amino acid residues. Herein, also the term parent insulin or parent insulin analogue is used for the insulin analogue. Mainly, the term parent is used when differentiating from an insulin analogue carrying a side chain which, for example, can be introduced chemically by acylation.

Herein terms like A1, A2, A3 etc. indicates the position 1, 2 and 3, respectively, in the A chain of insulin (counted from the N-terminal end). Similarly, terms like B1, B2, B3 etc. indicates the position 1, 2 and 3, respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are AlaA21, GlyA21 and GlnA21, respectively.

Herein terms like desB29 and desB30 indicate an insulin analogue lacking the B29 or B30 amino acid residue, respectively.

The numbering of the positions in the A and B chains in insulin analogues is done so that there is the largest identity between the amino acid residues present in the positions with the same numbers in the insulin analogue and in human insulin.

Herein, the term amino acid residue covers an amino acid from which a hydrogen atom has been removed from an amino group and/or a hydroxy group has been removed from a carboxy group and/or a hydrogen atom has been removed from a mercapto group. Imprecise, an amino acid residue may be designated an amino acid.

Herein, the expression "codable" in connection with terms like amino acid, amino acid residue, peptide or peptide residue is used to indicate an amino acid, amino acid residue, peptide or peptide residue which can be coded for by a triplet ("codon") of nucleotides, vide genetic engineering.

Herein, the term mutation covers any change in amino acid sequence (substitutions and insertions with codable amino acids as well as deletions).

Unless indicated explicitly, the amino acids mentioned herein are L-amino acids.

With fast acting insulin is meant an insulin having a faster onset of action than normal or regular human insulin.

With prolonged action profile in connection with insulin as well as the term basal insulin is meant an insulin having a longer duration of action than normal or regular human insulin.

By high physical stability is meant a tendency to fibrillation being less than 50% of that of human insulin. Fibrillation may be described by the lag time before fibril formation is initiated at a given conditions.

A polypeptide with insulin receptor and IGF-1 receptor affinity is a polypeptide which is capable of interacting with an insulin receptor and a human IGF-1 receptor in a suitable binding assay. Such receptor assays are well-know within the field and are further described in the examples. The acylated insulins of this invention will not bind to the IGF-1 receptor or will have a rather low affinity to said receptor. More precisely, the acylated insulins of this invention will have an affinity towards the IGF-1 receptor of substantially the same magnitude or less as that of human insulin.

For the sake of convenience, here follows the names of amino acids with the usual three letter codes & one letter codes in parenthesis: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If, due to typing errors, there are deviations from the commonly used codes, the commonly used codes apply. The amino acids present in the insulins of this invention are, preferably, amino acids which can be coded for by a nucleic acid. Amino acids like Glu and Asp can be in the $\alpha$, $\gamma$, L or D form.

The following abbreviations have been used in the specification and examples: Da is Dalton (molecular weight), kDa is kilo-Dalton (=1000 Da), Mw is molecular weight, OSu is 1-succinimidyloxy =2,5-dioxopyrrolidin-1-yloxy, RT is room temperature, SA is sinapinic acid and Su is 1-succinimidyl=2,5-dioxopyrrolidin-1-yl, TFA is trifluoroacetic acid, DCM is dichloromethane, NMP is N-methylpyrrolidinone (1-methyl-2-pyrrolodinone), tBu is tert-butyl, OTBU is tert-butoxy, DIEA (and DIPEA) is N,N-diisopropylethylamine, TSTU is N,N,N',N'-tetramethyl-O—(N-succinimidyluronium tetrafluoroborate, Tris is tris(hydroxymethyl)aminomethane, CV is column volume, OEG is the amino acid 8-amino-3,6-dioxaoctanoic acid, HSA is human serum albumin, TNBS is 2,4,6-trinitrobenzenesulfonic acid, HOBT (or HOBt) is 1-hydroxybenzotriazole. HOAt is 1-hydroxy-7-azabenzotriazole, NaOH is sodium hydroxyide, DMF is N,N-dimethyl formamide, THF is tetrahydrofuran, TFA is trifluoroacetic acid, mmol is millimoles, Fmoc is fluoren-9-ylmethoxycarbonyl, OEG is 8-amino-3,6-dioxaoctanoic acid (or a residue thereof), gGlu (herein also designated yGlu) is gamma-glutamic acid, and in example 11, for convenience, the following annotations are used to specify the sequence of the acyl moieties of the insulins of the invention and of the prior art: C16 is hexadecanedioyl, C17 is heptadecanedioyl, C18 is octadecanedioyl, C20 is eicosanedioyl, gGlu is gamma-glutamic acid, PEG3 is 3-(2-{2-[2-(2-aminoethoxy)-ethoxy]ethoxy}ethoxy)propionic acid, PEG5 is 3-{2-[2-(2-{2-[2-(2-aminoethoxy)ethoxy]ethoxy}ethoxy)-ethoxy]ethoxy}propionic acid and PEG7 is 3-[2-(2-{2-[2-(2-{2-[2-(2-aminoethoxy)ethoxy]ethoxy}-ethoxy)ethoxy]ethoxy}ethoxy)ethoxy]propionic acid (the complete structures/sequences can be found in the examples).

OBJECTS OF THIS INVENTION

The object of this invention is to overcome or ameliorate at least one of the disadvantages of the prior art, or to provide a useful alternative.

One object of this invention is to furnish insulin derivatives which have good bioavailability.

An aspect of this invention is to improve the absorption of insulins through human tissues.

Another object of this invention is to furnish insulin derivatives which can be administered pulmonary.

Another aspect of this invention is to improve the in vivo half-life of insulins.

Another aspect of this invention is to find insulin derivatives with increased potency Another aspect of this invention is to find insulin derivatives having a satisfactory physical stability.

Another aspect of this invention is to find insulin derivatives having a satisfactory chemical stability.

Another aspect of this invention is to find insulin derivatives having a satisfactory proteolytic stability.

Another aspect of this invention is to find insulin derivatives having a satisfactory solubility.

Another object of this invention is to furnish insulin derivatives having a prolonged action profile.

Another object of this invention is to furnish insulin derivatives, which are usable as basal insulins.

Another object of this invention is to furnish insulin derivatives, which have high insulin receptor binding affinities.

SUMMARY OF THIS INVENTION

Briefly, this invention relates to an acylated insulin wherein an acyl moiety is attached to the parent insulin and wherein said acyl moiety comprises repeating units of alkylene glycol containing amino acids. In another aspect, this invention relates to an acylated insulin, wherein the acyl moiety is a group of the general formula (I): Acy-AA1$_n$-AA2$_m$-AA3$_p$-, wherein n is 0 or an integer in the range 1-3, m is 0 or an integer in the range 1-6, p is an integer in the range 2-30, Acy is a fatty acid or a fatty diacid comprising 8 to 24 carbon atoms from which, formally, a hydroxy group has been removed from the carboxy group, AA1 is a neutral cyclic amino acid from which, formally, a hydroxy group has been removed from the carboxy group and, formally, a hydrogen atom has been removed from the amino group, AA2 is an acidic amino acid from which, formally, a hydroxy group has been removed from the carboxy group and, formally, a hydrogen atom has been removed from the amino group, AA3 is a neutral, alkyleneglycol-containing amino acid from which, formally, a hydroxy group has been removed from the carboxy group and, formally, a hydrogen atom has been removed from the amino group, and the connections between Acy, AA1, AA2 and/or AA3 are amide (peptide) bonds.

DESCRIPTION OF THE PREFERRED EMBODIMENTS

Surprisingly, the acylated insulins of this invention show a good bioavailability.

The acylated insulins of this invention can, formally be build from an insulin and an acyl moiety comprising repeating units of alkylene glycol containing amino acids having the collective formula (I), i.e., Acy-AA1$_n$-AA2$_m$-AA3$_p$-, wherein Acy, AA1, AA2, AA3, n, m and p are as defined herein (e.g., by formally removing a hydrogen atom from an amino group in the insulin and attaching the side chain of formula (I) thereto).

In the acylated insulins of this invention, the acyl moiety comprising repeating units of alkylene glycol containing amino acids and having the formula (I) is connected to an epsilon amino group in a lysine residue which is present in the parent insulin. For example, the acyl moiety comprising repeating units of alkylene glycol containing amino acids and having the formula (I) may be connected to a lysine residue in position B29 or B30 of the parent insulin.

The acyl group present in the group of the formula (I), i.e., Acy-AA1$_n$-AA2$_m$-AA3$_p$-, originates from a fatty acid or a fatty diacid.

Herein, the term "fatty acid" covers a linear or branched, aliphatic carboxylic acids having at least two carbon atoms and being saturated or unsaturated. Non limiting examples of fatty acids are myristic acid, palmitic acid, and stearic acid.

Herein, the term "fatty diacid" covers a linear or branched, aliphatic dicarboxylic acids having at least two carbon atoms and being saturated or unsaturated. Non limiting examples of fatty diacids are succinic acid, hexanedioic acid, octanedioic acid, decanedioic acid, dodecanedioic acid, tetradecanedioic acid, hexadecanedioic acid, heptadecanedioic acid, octadecanedioic acid, and eicosanedioic acid.

As mentioned herein, the order in which AA1, AA2 and AA3 appears in the acyl moiety with the formula (I) (Acy-AA1$_n$-AA2$_m$-AA3$_p$-) can be interchanged independently. Consequently, the formula Acy-AA1$_n$-AA2$_m$-AA3$_p$-) also covers moieties like, e.g., the formula Acy-AA2$_m$-AA1$_n$-AA3$_p$- and the formula Acy-AA3$_p$-AA2$_m$-AA1$_n$-, wherein Acy, AA1, AA2, AA3, n, m and p are as defined herein.

The neutral cyclic amino acid related to the moiety designated AA1 is an amino acid containing a saturated 6-membered carbocyclic ring, optionally containing a nitrogen heteroatom, and, preferably, the ring is a cyclohexane ring or a piperidine ring. Preferably, the molecular weight of this neutral cyclic amino acid is in the range from about 100 to about 200 Da.

The acidic amino acid related to the moiety designated AA2 is an amino acid with a molecular weight of up to about 200 Da comprising two carboxylic acid groups and one primary or secondary amino group.

The neutral, alkyleneglycol-containing amino acid related to the moiety designated AA3 is an alkyleneglycol moiety, optionally an oligo- or polyalkyleneglycol moiety containing a carboxylic acid functionality at one end and a amino group functionality at the other end.

Herein, the term alkyleneglycol moiety covers oligo- and polyalkyleneglycol moieties as well as monoalkyleneglycol moieties. Polyalkyleneglycols comprises polyethyleneglycol based, polypropylene-glycol based and polybutyleneglycol based chains, i.e., chains that are based on the repeating unit —CH$_2$CH$_2$O—, —CH$_2$CH$_2$CH$_2$O— or —CH$_2$CH$_2$CH$_2$CH$_2$O—. The alkyleneglycol moiety can be monodisperse (with well defined length/molecular weight) as well as polydisperse (with less well defined length/average molecular weight). Monoalkyleneglycol moieties comprises —OCH$_2$CH$_2$O—, —OCH$_2$CH$_2$CH$_2$O— or —OCH$_2$CH$_2$CH$_2$CH$_2$O— containing different groups at each end.

The connections between the moieties Acy, AA1, AA2 and/or AA3 are formally obtained by amide bond (peptide bond) formation (—CONH—).

Specific examples of the parent insulin present in the acylated insulins of this invention are the following (with the proviso that, here, a hydrogen atom has been added to the amino group): human insulin; desB30 human insulin; B28D human insulin; B28D, desB30 human insulin; B28K, B29P human insulin and B3K, B29E human insulin.

Specific examples of acyl moieties of the formula Acy-AA1$_n$-AA2$_m$-AA3$_p$-attached to the epsilon amino group in a lysine residue which is present in the parent insulin present in an acylated insulin of this invention are the following:

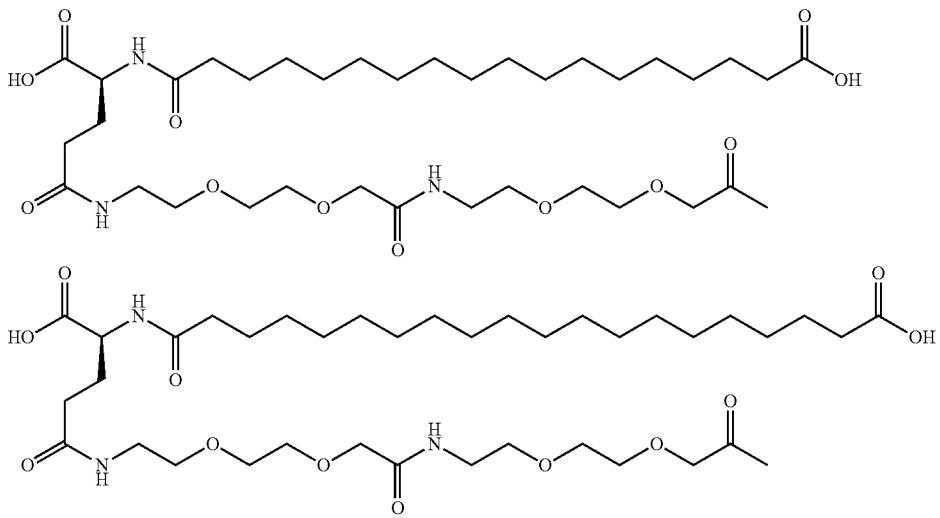

-continued
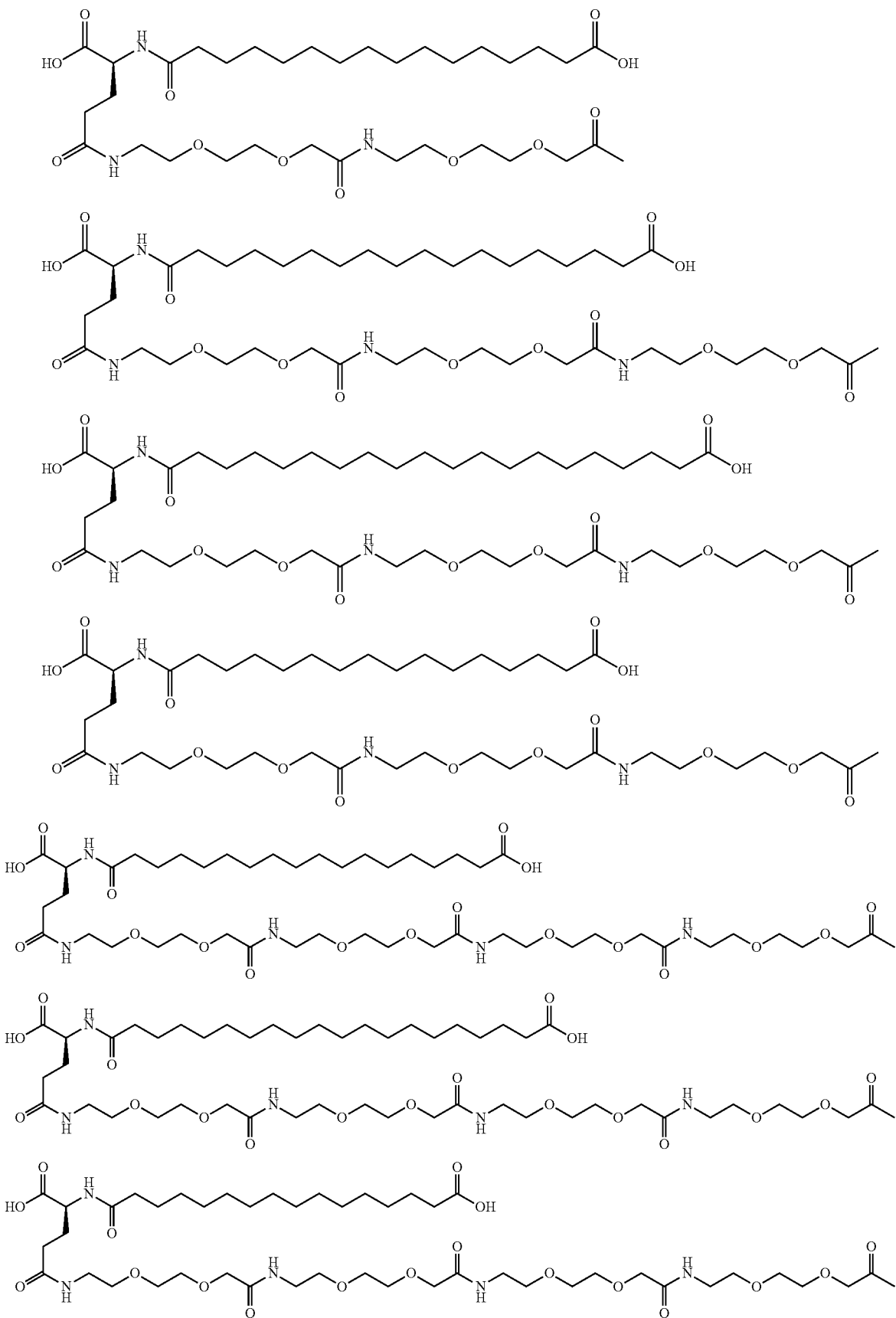

-continued
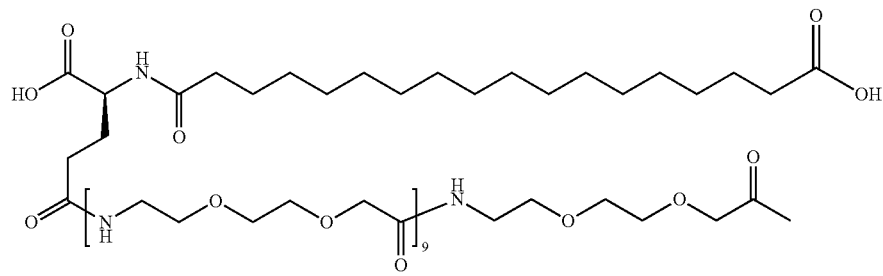
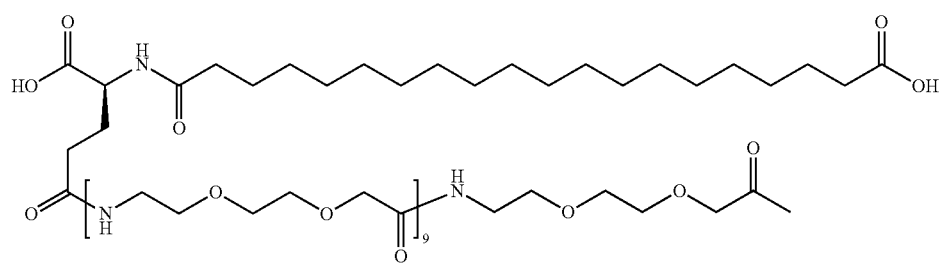
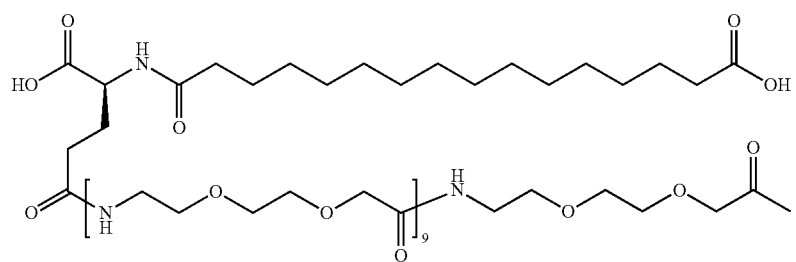
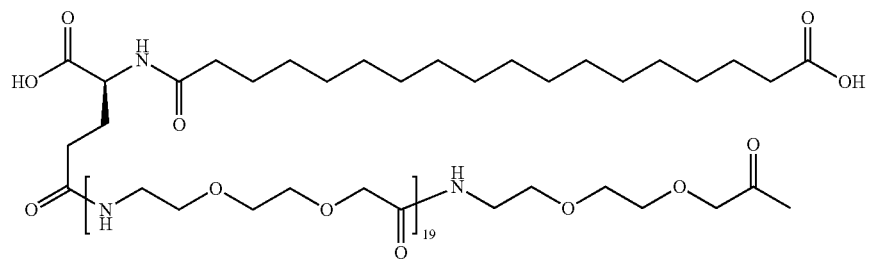
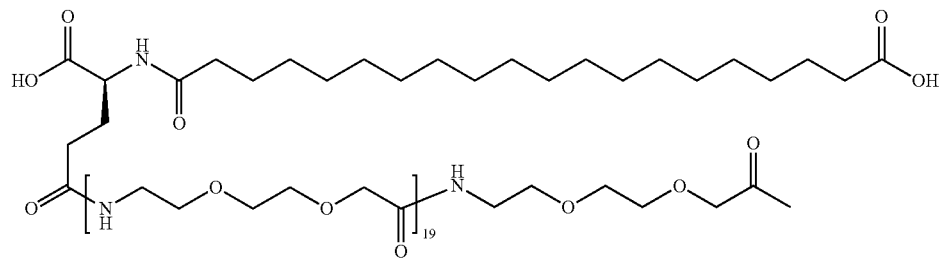
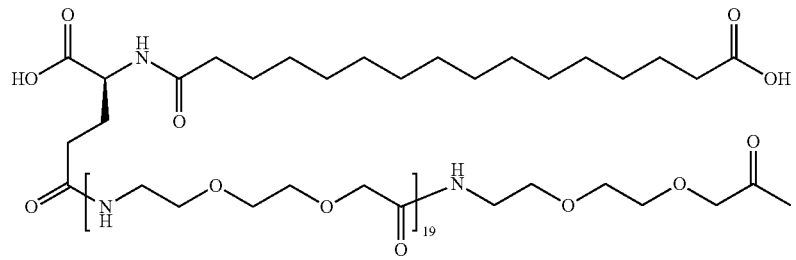

-continued
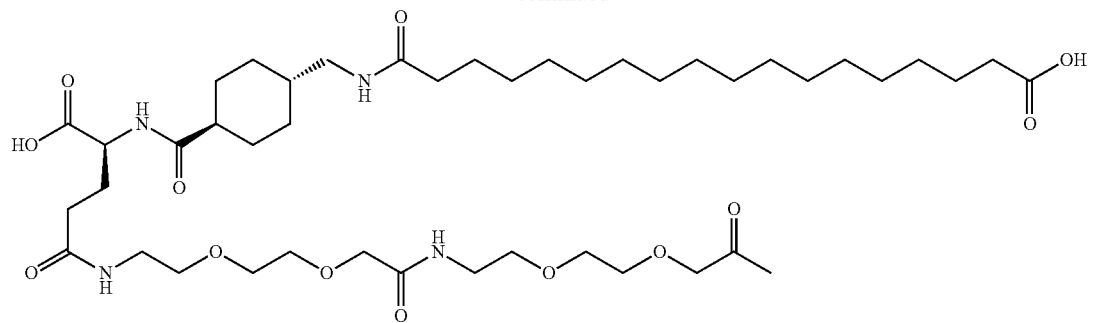
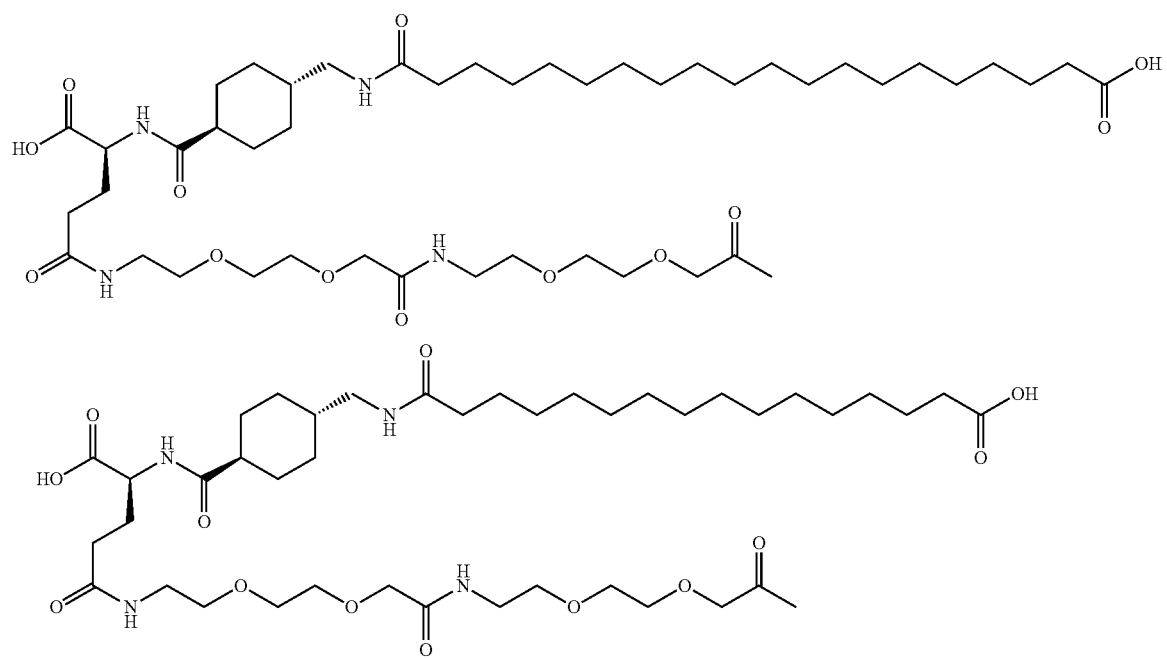
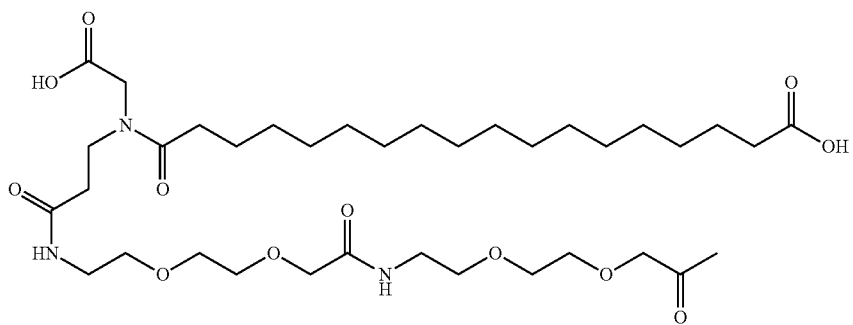
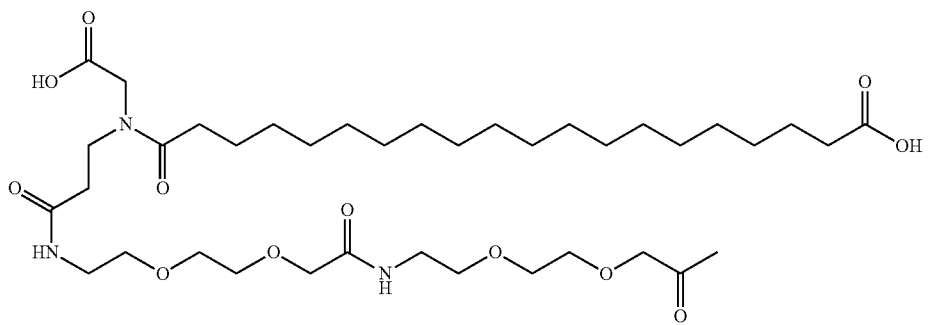

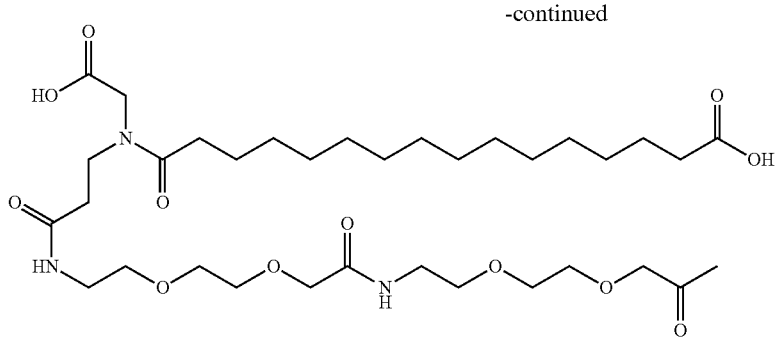

Any of the above non-limiting specific examples of acyl moieties of the formula (I) (Acy-AA1$_n$-AA2$_m$-AA3$_p$-) can be attached to an epsilon amino group of a lysine residue present in any of the above non-limiting specific examples of insulins thereby giving further specific examples of acylated insulins of this invention.

The parent insulins can be prepared in a manner known per se. For example, they can be produced by expressing a DNA sequence encoding the single-chain insulin in question in a suitable host cell by well known technique as disclosed in e.g., EP 1,246,845. The insulin is expressed in a transformed host cell as a precursor molecule which is converted into the desired insulin molecule by enzymatic and chemical in vitro processes as disclosed in, e.g., EP 163,529 and EP 214,826. The precursor molecule may be expressed with an N-terminal extension which is later cleaved of as disclosed in, e.g., EP 1246,845. Examples of N-terminal extensions of the type suitable in the present invention are, e.g., disclosed in U.S. Pat. No. 5,395,922 and EP patent No. 765,395. More specifically, reference can be made to WO 2006/082205, from page 37, line 31, to page 39, line 29.

Acylated insulins of this invention may be provided in the form of essentially zinc free compounds or in the form of zinc complexes. When zinc complexes of an acylated insulin of this invention are provided, two $Zn^{2+}$ ions, three $Zn^{2+}$ ions or four $Zn^{2+}$ ions can be bound to each insulin hexamer. Solutions of zinc complexes of the acylated insulins of this invention will contain mixtures of such species.

In a further aspect, this invention relates to a pharmaceutical composition comprising a therapeutically effective amount of an acylated insulin of this invention together with a pharmaceutically acceptable carrier which can be used for the treatment of type 1 diabetes, type 2 diabetes and other states that cause hyperglycaemia in patients in need of such a treatment. An acylated insulin of this invention can be used for the manufacture of a pharmaceutical composition for use in the treatment of type 1 diabetes, type 2 diabetes and other states that cause hyperglycaemia. Such compositions are prepared in a manner known per se.

In a further aspect of this invention, there is provided a pharmaceutical composition for treating type 1 diabetes, type 2 diabetes and other states that cause hyperglycaemia in a patient in need of such a treatment, comprising a therapeutically effective amount of an acylated insulins of this invention in mixture with an insulin or an insulin analogue which has a rapid onset of action, together with pharmaceutically acceptable carriers and additives.

In a further aspect, this invention relates to a pulmonary application for treating type 1 diabetes, type 2 diabetes and other states that cause hyperglycaemia in a patient in need of such a treatment, comprising a therapeutically effective amount of an acylated insulins of this invention, optionally in mixture with an insulin or an insulin analogue which has a rapid onset of action, together with pharmaceutically acceptable carriers and additives.

In one aspect, this invention provides a pharmaceutical composition being a mixture of an acylated insulin of this invention and a rapid acting insulin analogue selected from the group consisting of AspB28 human insulin; LysB28 ProB29 human insulin and LysB3 GluB29 human insulin.

The acylated insulins of this invention and the rapid acting insulin analogue can be mixed in a ratio of about 90/10%; about 70/30% or about 50/50%.

In a further aspect of the invention, there is provided a method of treating type 1 diabetes, type 2 diabetes and other states that cause hyperglycaemia in a patient in need of such a treatment, comprising administering to the patient a therapeutically effective amount of an acylated insulins of this invention together with a pharmaceutically acceptable carrier and pharmaceutical acceptable additives.

In a further aspect of the invention, there is provided a method of treating type 1 diabetes, type 2 diabetes and other states that cause hyperglycaemia in a patient in need of such a treatment, comprising administering to the patient a therapeutically effective amount of an acylated insulins of this invention in mixture with an insulin or an insulin analogue which has a rapid onset of action, together with a pharmaceutically acceptable carrier and pharmaceutical acceptable additives.

In a further aspect of the invention there is provided a pharmaceutical composition for the treatment of diabetes in a patient in need of such treatment, comprising a therapeutically effective amount of an acylated insulins of this invention in mixture with an insulin or an insulin analogue which has a rapid onset of action, together with a pharmaceutically acceptable carrier.

In a further aspect of the invention there is provided a pharmaceutical composition according to the invention intended for pulmonal administration.

In a further aspect of the invention there is provided a method of treating diabetes in a patient in need of such a treatment, comprising administering to the patient a therapeutically effective amount of an acylated insulins according to claim 1 together with a pharmaceutically acceptable carrier.

In a further aspect of the invention there is provided a method of treating diabetes in a patient in need of such a treatment, comprising administering to the patient a therapeutically effective amount of an acylated insulins according to claim 1 in mixture with an insulin or an insulin analogue which has a rapid onset of action, together with a pharmaceutically acceptable carrier.

In a further aspect, the present invention relates to acylated insulins of this invention which have insulin receptor binding affinities as described herein, measured in presence of HSA (for example in presence of 0.5%, 1%, 1.5%, 2%, 2.5%, 3%, 3.5%, 4%, or 4.5% HSA), that are >1%, more preferred >1.2%, more preferred >1.5%, more preferred >1.75% relative to human insulin.

In a further aspect, the present invention relates to acylated insulins of this invention which have potencies determined in the rat clamp experiment described herein that are >40%, more preferred >45%, more preferred >50%, more preferred >55%, more preferred >60%, more preferred >65%, more preferred >70%, more preferred >75% relative to human insulin.

In a further aspect, the present invention relates to acylated insulins of this invention which have an overall hydrophobicity which is essentially similar to that of human insulin.

In a further aspect, the acylated insulins of this invention have a hydrophobic index, $k'_{rel}$, which is in the range from about 0.02 to about 10, from about 0.1 to about 5; from about 0.5 to about 5; from about 0.2 to about 2; from about 0.2 to about 1; from about 0.1 to about 2; or from about 0.5 to about 2. The hydrophobicity (hydrophobic index) of the acylated insulins of this invention relative to human insulin, $k'_{rel}$, was measured on a LiChrosorb RP18 (5 μm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least $2t_0$ by varying the ratio between the A and B solutions. $k'_{rel}=(t_{derivative}-t_0)/(t_{human}-t_0)$.

In another aspect, the invention relates to a pharmaceutical composition comprising an acylated insulin of this invention which is soluble at physiological pH values.

In another aspect, the invention relates to a pharmaceutical composition comprising an acylated insulin of this invention which is soluble at pH values in the interval from about 6.5 to about 8.5.

In another aspect, the invention relates to a pharmaceutical composition with a prolonged profile of action which comprises an acylated insulin of this invention.

In another aspect, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an acylated insulins of this invention or of a mixture of an acylated insulins of this invention together with a rapid acting insulin analogue.

Use of the Compounds of this Invention

The route of administration may be any route which effectively transports a compound of this invention to the desired or appropriate place in the body, such as parenterally, for example, subcutaneously, intramuscularly or intraveneously. Alternatively, a compound of this invention can be administered orally, pulmonary, or nasally.

For parenteral administration, a compound of this invention is formulated analogously with the formulation of known insulins. Furthermore, for parenteral administration, a compound of this invention is administered analogously with the administration of known insulins and the physicians are familiar with this procedure.

Parenteral administration can be performed by means of a syringe, optionally a pen-like syringe. Alternatively, parenteral administration can be performed by means of an infusion pump.

Injectable compositions of a compound of this invention can be prepared using the conventional techniques of the pharmaceutical industry which involve dissolving and mixing the ingredients as appropriate to give the desired end product. Thus, according to one procedure, a compounds of this invention is dissolved in an amount of water which is somewhat less than the final volume of the composition to be prepared. An isotonic agent, a preservative and a buffer is added as required and the pH value of the solution is adjusted—if necessary—using an acid, for example, hydrochloric acid, or a base, for example, aqueous sodium hydroxide, as needed. Finally, the volume of the solution is adjusted with water to give the desired concentration of the ingredients.

More precisely, an insulin preparation of this invention, for example a solution or suspension, may be prepared by dissolving a compound of this invention in an aqueous medium at slightly acidic conditions, for example, in a concentration in the range from about 240 to about 1200 nmole/ml. The aqueous medium is made isotonic, for example, with sodium chloride or glycerol. Furthermore, the aqueous medium may contain zinc ions in a concentrations of up to about 20 μg of $Zn^{++}$ per unit of insulin activity, buffers such as acetate and citrate and preservatives such as m-cresol or phenol. The pH value of the solution is adjusted towards neutrality without getting too close to the isoelectric point of the compound of this invention in order to avoid precipitation. The pH value of the final insulin preparation depends upon the number of charges that, optionally, have been changed in the compound of this invention, the concentration of zinc ions, the concentration of the compound of this invention and the compound of this invention selected. The insulin preparation is made sterile, for example, by sterile filtration.

The insulin preparations of this invention are used similarly to the use of the known insulin preparations.

The amount of a compound of this invention to be administered, the determination of how frequently to administer a compound of this invention, and the election of which compound or compounds of this invention to administer, optionally together with another antidiabetic compound, is decided in consultation with a practitioner who is familiar with the treatment of diabetes. Hence, this invention also relates to a method of treating diabetes, comprising administering an affective amount of a compound of this invention to a patient in need of such treatment.

Pharmaceutical Compositions

The acylated insulins of this invention may be administered subcutaneously, orally, or pulmonary.

For subcutaneous administration, the acylated insulins of this invention are formulated analogously with the formulation of known insulins. Furthermore, for subcutaneous administration, the acylated insulins of this invention are administered analogously with the administration of known insulins and, generally, the physicians are familiar with this procedure.

Acylated insulins of this invention may be administered by inhalation in a dose effective to increase circulating insulin levels and/or to lower circulating glucose levels. Such administration can be effective for treating disorders such as diabetes or hyperglycemia. Achieving effective doses of insulin requires administration of an inhaled dose in the range from about 0.5 μg/kg to about 50 μg/kg of an acylated insulin of this invention. A therapeutically effective amount can be determined by a knowledgeable practitioner, who will take into account factors including insulin level, blood glucose levels, the physical condition of the patient, the patient's pulmonary status, or the like.

The acylated insulins of this invention may be delivered by inhalation to achieve slow absorption and/or reduced systemical clearance thereof. Different inhalation devices typically provide similar pharmacokinetics when similar particle sizes and similar levels of lung deposition are compared.

The acylated insulins of this invention may be delivered by any of a variety of inhalation devices known in the art for administration of a therapeutic agent by inhalation. These devices include metered dose inhalers, nebulizers, dry powder generators, sprayers, and the like. Preferably, the acylated insulins of this invention are delivered by a dry powder inhaler or a sprayer. There are several desirable features of an inhalation device for administering acylated insulins of this invention. For example, delivery by the inhalation device is advantageously reliable, reproducible, and accurate. The inhalation device should deliver small particles or aerosols, e.g., less than about 10 µm, for example about 1-5 µm, for good respirability. Some specific examples of commercially available inhalation devices suitable for the practice of this invention are Cyclohaler, Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of acylated insulins of this invention, the quantity of the formulation delivered and the duration of administration of a single dose depend on the type of inhalation device employed. For some aerosol delivery systems, such as nebulizers, the frequency of administration and length of time for which the system is activated will depend mainly on the concentration of the acylated insulin of this invention in the aerosol. For example, shorter periods of administration can be used at higher concentrations of the acylated insulin of this invention in the nebulizer solution. Devices such as metered dose inhalers can produce higher aerosol concentrations, and can be operated for shorter periods of time to deliver the desired amount of an acylated insulin of this invention. Devices such as powder inhalers deliver active agent until a given charge of agent is expelled from the device. In this type of inhaler, the amount of insulin acylated insulins of this invention in a given quantity of the powder determines the dose delivered in a single administration.

The particle size of acylated insulins of this invention in the formulation delivered by the inhalation device is critical with respect to the ability of insulin to make it into the lungs, and preferably into the lower airways or alveoli. Preferably, the acylated insulins of this invention is formulated so that at least about 10% of the acylated insulin of this invention delivered is deposited in the lung, preferably about 10 to about 20%, or more. Particles of the acylated insulin delivered by inhalation have a particle size preferably less than about 10 µm, more preferably in the range of about 1 µm to about 5 µm. The formulation of the acylated insulin is selected to yield the desired particle size in the chosen inhalation device.

Advantageously for administration as a dry powder, an acylated insulin of this invention is prepared in a particulate form with a particle size of less than about 10 µm, preferably about 1 to about 5 µm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 µm. Such formulations can be achieved by spray drying, milling, micronisation, or critical point condensation of a solution containing an acylated insulin of this invention and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of acylated insulins of this invention for administration from a dry powder inhaler typically include a finely divided dry powder containing the derivative, but the powder can also include a bulking agent, carrier, excipient, another additive, or the like. Additives can be included in a dry powder formulation of an acylated insulin, e.g., to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The acylated insulin can be mixed with an additive at a molecular level or the solid formulation can include particles of an acylated insulin mixed with or coated on particles of the additive. Typical additives include mono-, di-, and polysaccharides; sugar alcohols and other polyols, such as, e.g., lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the acylated insulins of this invention can be produced by forcing a suspension or solution of an acylated insulin through a nozzle under pressure. The nozzle size and configuration, the applied pressure, and the liquid feed rate can be chosen to achieve the desired output and particle size. An electrospray can be produced, e.g., by an electric field in connection with a capillary or nozzle feed. Advantageously, particles of insulin conjugate delivered by a sprayer have a particle size less than about 10 µm, preferably in the range of about 1 µm to about 5 µm.

Formulations of acylated insulins of this invention suitable for use with a sprayer will typically include the acylated insulin of this invention in an aqueous solution at a concentration of from about 1 mg to about 500 mg of an acylated insulin per ml of solution. Depending on the acylated insulin chosen and other factors known to the medical advisor, the upper limit may be lower, e.g., 450, 400, 350, 300, 250, 200, 150, 120, 100 or 50 mg of the acylated insulin per ml of solution. The formulation can include agents such as an excipient, a buffer, an isotonicity agent, a preservative, a surfactant, and, preferably, zinc. The formulation can also include an excipient or agent for stabilization of the acylated insulin, such as a buffer, a reducing agent, a bulk protein, or a carbohydrate. Bulk proteins useful in formulating insulin conjugates include albumin, protamine, or the like. Typical carbohydrates useful in formulating the acylated insulin include sucrose, mannitol, lactose, trehalose, glucose, or the like. A formulation of an acylated insulin of this invention can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing an acylated insulin of this invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump.

Injectable compositions of the acylated insulins of this invention can be prepared using the conventional techniques of the pharmaceutical industry which involve dissolving and mixing the ingredients as appropriate to give the desired end product. Thus, according to one procedure, an acylated insulin is dissolved in an amount of water which is somewhat less than the final volume of the composition to be prepared. Zink, an isotonic agent, a preservative and/or a buffer is/are added as required and the pH value of the solution is adjusted—if necessary—using an acid, e.g., hydrochloric acid, or a base, e.g., aqueous sodium hydroxide as needed. Finally, the volume of the solution is adjusted with water to give the desired concentration of the ingredients.

In a further embodiment of this invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinic acid, maleic acid, fumaric acid, tartaric acid, aspartic acid or mixtures thereof. Each one of these specific buffers constitutes an alternative embodiment of this invention.

In a further embodiment of this invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(4-chlorophenoxy)-1,2-propanediol) or mixtures thereof. In a further embodiment of this invention the preservative is present in a concentration from about 0.1 mg/ml to 20 mg/ml. In a further embodiment of this invention the preservative is present in a concentration from about 0.1 mg/ml to 5 mg/ml. In a further embodiment of this invention the preservative is present in a concentration from about 5 mg/ml to 10 mg/ml. In a further embodiment of this invention the preservative is present in a concentration from about 10 mg/ml to 20 mg/ml. Each one of these specific preservatives constitutes an alternative embodiment of this invention. The use of a preservative in pharmaceutical compositions is well-known to the skilled person. For convenience reference is made to Remington: *The Science and Practice of Pharmacy*, 19$^{th}$ edition, 1995.

In a further embodiment of this invention, the formulation further comprises an isotonic agent which may be selected from the group consisting of a salt (e.g., sodium chloride), a sugar or sugar alcohol, an amino acid (for example, L-glycine, L-histidine, arginine, lysine, isoleucine, aspartic acid, tryptophan or threonine), an alditol (e.g. glycerol (glycerine), 1,2-propanediol (propyleneglycol), 1,3-propanediol or 1,3-butanediol), polyethyleneglycol (e.g., PEG400) or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, e.g., mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of this invention. In one embodiment, the sugar or sugar alcohol concentration is between about 1 mg/ml and about 150 mg/ml. In a further embodiment of this invention the isotonic agent is present in a concentration from about 1 mg/ml to 50 mg/ml. In a further embodiment of this invention the isotonic agent is present in a concentration from about 1 mg/ml to 7 mg/ml. In a further embodiment of this invention the isotonic agent is present in a concentration from about 8 mg/ml to 24 mg/ml. In a further embodiment of this invention the isotonic agent is present in a concentration from about 25 mg/ml to 50 mg/ml. Each one of these specific isotonic agents constitutes an alternative embodiment of this invention. The use of an isotonic agent in pharmaceutical compositions is well-known to the skilled person. For convenience reference is made to Remington: *The Science and Practice of Pharmacy*, 19$^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an acylated insulins of this invention may, e.g., be prepared as described in European Patent No. 272097.

Compositions containing acylated insulins of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the acylated insulin of this invention be determined for each individual patient by those skilled in the art in a similar way as for known insulin compositions.

IMPORTANT FEATURES OF THIS INVENTION

To sum up, some features of this invention are as follows:
1. An acylated insulin wherein an acyl moiety is attached to the parent insulin via an amide bond (—CONH—) and wherein said acyl moiety comprises repeating units of alkylene glycol containing amino acids and wherein there is only one lysine residue (K & Lys) in the parent insulin, said acyl moiety being connected to an epsilon amino group in said lysine residue.

2. An acylated insulin, according to clause 1, wherein the acyl moiety is a group of the general formula (I):

wherein
n is 0 or an integer in the range 1-3,
m is 0 or an integer in the range 1-6,
p is an integer in the range 2-30
Acy is a fatty acid or a fatty diacid comprising 8 to 24 carbon atoms from which, formally, a hydroxy group has been removed from the fatty acid and, formally, a hydroxy group has been removed from one of the carboxy groups in the fatty diacid,
AA1 is a neutral cyclic amino acid from which, formally, a hydroxy group has been removed from the carboxy group and a hydrogen atom has been removed from the amino group,
AA2 is an acidic amino acid from which, formally, a hydroxy group has been removed from the carboxy group and a hydrogen atom has been removed from the amino group,
AA3 is a neutral, alkyleneglycol-containing amino acid from which, formally, a hydroxy group has been removed from the carboxy group and a hydrogen atom has been removed from the amino group,
the order in which AA1, AA2 and AA3 appears in the group of formula I can be interchanged independently,
the connections between Acy, AA1, AA2 and/or AA3 being amide (peptide) bonds.

3. An acylated insulin, according to clause 1, wherein the acyl moiety is a group of the general formula (I):

wherein
n is 0 or an integer in the range 1-3,
m is 0 or an integer in the range 1-6,
p is an integer in the range 2-30
Acy is a fatty acid or a fatty diacid comprising 8 to 24 carbon atoms from which, formally, a hydroxy group has been removed from the fatty acid and, formally, a hydroxy group has been removed from one of the carboxy groups in the fatty diacid,
AA1 is a neutral cyclic amino acid from which, formally, a hydroxy group has been removed from the carboxy group and a hydrogen atom has been removed from the amino group,
AA2 is an acidic amino acid from which, formally, a hydroxy group has been removed from the carboxy group and a hydrogen atom has been removed from the amino group,
AA3 is a neutral, alkyleneglycol-containing amino acid from which, formally, a hydroxy group has been removed from the carboxy group and a hydrogen atom has been removed from the amino group,
the connections between Acy, AA1, AA2 and/or AA3 being amide (peptide) bonds.

4. An acylated insulin, according to any one of the preceding, possible clauses, wherein n is 0 or 1.
5. An acylated insulin, according to any one of the preceding, possible clauses, wherein m is 1.
6. An acylated insulin, according to any one of the preceding, possible clauses, wherein p is in the range 2 to 20, preferably in the range 2 to 10, more preferred in the range 2 to 4, and, specifically 2, 3, 4, 10, 20 or 30.
7. An acylated insulin, according to any one of the preceding, possible clauses, wherein the acyl moiety is a group of the general formula (I) has one of the general formulae: Acy-AA1-AA2-AA3-AA3-, Acy-AA2-AA3-AA3-, Acy-AA2-AA3-AA3-AA3-, Acy-AA2-AA3-AA3-AA3-AA3- or Acy-A3-M3-AA2, wherein Acy, AA1, AA2 and AA3 each is as defined herein.

8. An acylated insulin, according to any one of the preceding, possible clauses, wherein Acy contains14 to 20 carbon atoms, preferably 16 to 20 carbon atoms, more preferred 16 to 18 carbon atoms, alternatively 18 to 20 carbon atoms and specifically 10, 12, 14, 16, 17, 18, 20 or 22 carbon atoms.

9. An acylated insulin, according to any one of the preceding, possible clauses, wherein Acy contains 16 to 20 carbon atoms.

10. An acylated insulin, according to any one of the preceding, possible clauses, wherein Acy is a fatty diacid from which, formally, a hydroxy group has been removed from one of the carboxy groups.

11. An acylated insulin, according to any one of the preceding, possible clauses, wherein Acy is hexadecandioic acid, heptadecandioic acid, octadecandioic acid or eicosanedioic acid from which a hydroxy group has been removed from one of the carboxy groups.

12. An acylated insulin, according to any one of the preceding, possible clauses, wherein AA1 is

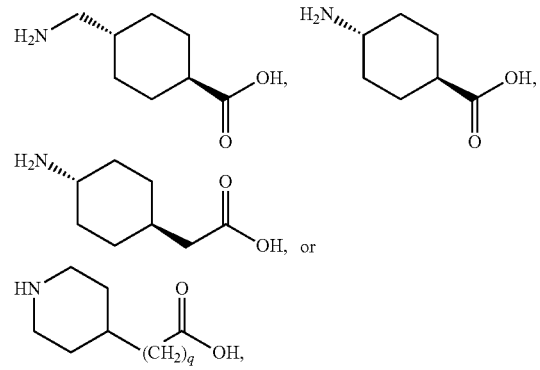

from which the hydroxy group is to be removed from the carboxy group and a hydrogen atom is to be removed from the amino group, and wherein q is 0, 1, 2, 3 or 4.

13. An acylated insulin, according to the preceding, possible clauses, wherein AA1 is

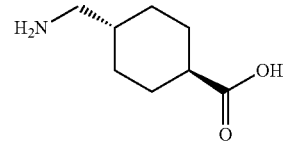 [SMILES: NC[C@H]1CC[C@H](C(=O)O)CC1]

from which a hydroxy group is to be removed from the carboxy group and a hydrogen atom is to be removed from the amino group.

14. An acylated insulin, according to any one of the preceding, possible clauses, wherein AA2 is Glu (α or γ, L or D), Asp (α or β, L or D),

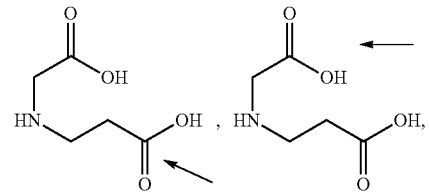

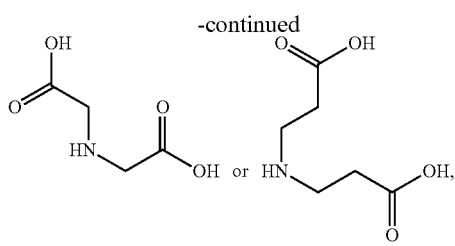

from which a hydroxy group is to be removed from the carboxy group and a hydrogen atom is to be removed from the amino group, and wherein the arrows indicate the attachment point to the amino group of AA2 or AA3.

15. An acylated insulin, according to any one of the preceding, possible clauses, wherein AA2 is γ-L-Glu (also noted as: γGlu) from which a hydroxy group is to be removed from the carboxy group and a hydrogen atom is to be removed from the amino group.

16. An acylated insulin, according to any one of the preceding, possible clauses, wherein AA3 is:

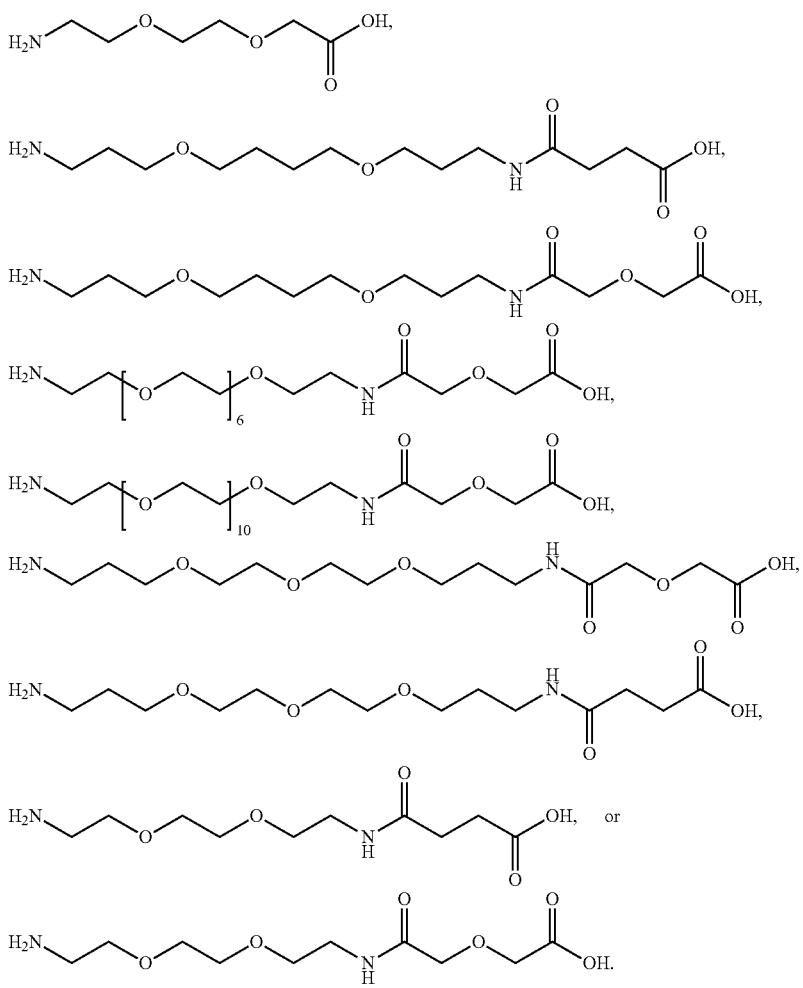

from which, formally, the hydroxy group is to be removed from the carboxy group and a hydrogen atom is to be removed from the amino group.

17. An acylated insulin, according to the preceding clause, wherein AA3 is:

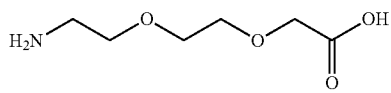 [SMILES: NCCOCCOCC(=O)O]

from which the hydroxy group is to be removed from the carboxy group and a hydrogen atom is to be removed from the amino group.

18. An acylated insulin, according to any one of the preceding, possible clauses, wherein the parent insulin is human insulin; desB30 human insulin; B28D human insulin; B28D, desB30 human insulin; B28K, B29P human insulin and B3K, B29E human insulin.

19. An acylated insulin, according to the preceding clause, wherein the parent insulin is human insulin; desB30 human insulin; B28D human insulin and B28D, desB30 human insulin.

20. An acylated insulin, according to the preceding clause, wherein the parent insulin is desB30 human insulin.

21. An acylated insulin, according to any one of the preceding, possible clauses, wherein the parent insulin consist of 51 amino acid residues.

22. An acylated insulin, according to any one of the preceding, possible clauses, wherein the parent insulin consist of 50 amino acid residues.
23. An acylated insulin, according to any one of the preceding, possible clauses, wherein the parent insulin is human insulin.
24. An acylated insulin, according to any one of the preceding, possible clauses, wherein the amino acid residue in position B3 of the parent insulin is K (Lys) and the amino acid residue in position B29 of the parent insulin is E (Glu).
25. An acylated insulin, according to any one of the preceding, possible clauses, wherein the amino acid residue in position B28 of the parent insulin is D (Asp).
26. An acylated insulin, according to any one of the preceding, possible clauses except the last one, wherein the amino acid in position B28 is K and the amino acid in position B29 is P.
27. An acylated insulin, according to any one of the preceding, possible clauses, wherein the amino acid residue in position B29 of the parent insulin is Lys.
28. An acylated insulin, according to any one of the preceding, possible clauses except the last one, wherein the amino acid residue in position B29 of the parent insulin is E or P (Glu or Pro).
29. An acylated insulin, according to any one of the preceding, possible clauses, wherein there is no amino acid residue in position B30 of the parent insulin (i.e. a desB30 insulin).
30. An acylated insulin, according to any one of the preceding, possible clauses, wherein all the amino acid residues in the parent insulin are residues of codable amino acids.
31. An acylated insulin, according to any one of the preceding, possible clauses, wherein only one of the amino acid residues in the parent insulin deviates from the amino acid residues present in human insulin.
32. An acylated insulin, according to any one of the preceding, possible clauses, wherein exactly two of the amino acid residues in the parent insulin deviates from the amino acid residues present in human insulin.
33. An acylated insulin, according to any one of the preceding, possible clauses, wherein exactly three of the amino acid residues in the parent insulin deviates from the amino acid residues present in human insulin.
34. An acylated insulin, according to any one of the preceding, possible clauses, wherein exactly four of the amino acid residues in the parent insulin deviates from the amino acid residues present in human insulin.
35. An acylated insulin according to any one of the preceding, possible product clauses for use as a medicament, for use in a medicament or for use in the preparation of a medicament.
36. An acylated insulin according to any one of the preceding, possible product clauses for treating diabetes or the use of an acylated insulin according to any one of the preceding, possible product clauses for the preparation of a medicament for the treatment of diabetes.
37. Any novel feature or combination of features described herein.

Combining one or more of the embodiments described herein, optionally also with one or more of the claims below, results in further embodiments and the present invention relates to all possible combinations of said embodiments and claims.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

The following examples are offered by way of illustration, not by limitation.

EXAMPLES

General procedures

Construction of Expression Vectors, Transformation of the Yeast Cells, and Expression of the Insulin Precursors of the Invention All expressions plasmids are of the C-POT type, similar to those described in EP 171142, which are characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90/10075) as are all sequences except the sequence of the EcoRI-XbaI fragment encoding the fusion protein of the leader and the insulin product. In order to express different fusion proteins, the EcoRI-XbaI fragment of pKFN1003 is simply replaced by an EcoRI-XbaI fragment encoding the leader-insulin fusion of interest. Such EcoRI-XbaI fragments may be synthesized using synthetic oligonucleotides and PCR according to standard techniques.

Yeast transformants were prepared by transformation of the host strain *S. cerevisiae* strain MT663 (MATalMATα pep-4-3/pep-4-3 HIS4/his4 tpi::LEU2/tpi::LEU2 Cir$^+$). The yeast strain MT663 was deposited in the Deutsche Sammlung von Mikroorganismen and Zellkulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM $Na_2EDTA$ pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM $Na_2EDTA$, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM $CaCl_2$, 10 mM Tris HCl (pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM $CaCl_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM $CaCl_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agarsolidified, sorbitol containing medium. S. cerevisiae strain MT663 transformed with expression plasmids was grown in YPD for 72 h at 30° C.

The following examples refer to intermediate compounds and final products identified in the specification and in the examples. The preparation of the insulin derivatives of this invention is described in detail using the following examples, but the chemical reactions and purification schemes described are disclosed in terms of their general applicability to the preparation of the insulin derivatives of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

The insulin derivatives of this invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

General Procedure for the Solid Phase Synthesis of Acylation Reagents of the General Formula (II):

(II): Acy-$AA1_n$-$AA2_m$-$AA3_p$—OSu, wherein Acy, AA1, AA2, AA3, n, m, and p are as defined above and OSu is 1-succinimidyloxy=2,5-dioxopyrrolidin-1-yloxy (ie. a N-hydroxysuccinimidyl ester).

Compounds according to this invention containing a group of the general formula II can be synthesised on solid support using procedures well known to skilled persons in the art of solid phase peptide synthesis. This procedure comprises attachment of a Fmoc protected amino acid to a polystyrene 2-chlorotritylchloride resin. The attachment can, e.g., be accomplished using the free N-protected amino acid in the presence of a tertiary amine, like triethyl amine or N,N-diisopropylethyl-amine (see references below). The C-terminal end (which is attached to the resin) of this amino acid is at the end of the synthetic sequence being coupled to the parent insulins of the invention. After attachment of the Fmoc amino acid to the resin, the Fmoc group is deprotected using, e.g., secondary amines, like piperidine or diethyl amine, followed by coupling of another (or the same) Fmoc protected amino acid and deprotection. The synthetic sequence is terminated by coupling of mono-tert-butyl protected fatty (α, ω)-diacids, like hexadecanedioic, heptadecanedioic, octadecanedioic or eicosanedioic acid mono-tert-butyl esters. Cleavage of the compounds from the resin is accomplished using diluted acid like 0.5-5% TFA/DCM (trifluoroacetic acid in dichloromethane), acetic acid (e.g., 10% in DCM, or HOAc/trifluoroethanol/DCM 1:1:8), or hexafluoroisopropanol in DCM (See, e.g., "Organic Synthesis on Solid Phase", F. Z. Dörwald, Wiley-VCH, 2000. ISBN 3-527-29950-5, "Peptides: Chemistry and Biology", N. Sewald & H.-D. Jakubke, Wiley-VCH, 2002, ISBN 3-527-30405-3 or "The Combinatorial Cheemistry Catalog" 1999, Novabiochem AG, and references cited therein). This ensures that tert-butyl esters present in the compounds as carboxylic acid protecting groups are not deprotected. Finally, the C-terminal carboxy group (liberated from the resin) is activated, e.g., as the N-hydroxysuccinimide ester (OSu) and used either directly or after purification as coupling reagent in attachment to parent insulins of the invention. This is illustrated in example 1.

General Procedure (A) for Preparation of Acylated, Extended Insulins of this Invention The general procedure (A) is outlined below and illustrated in the first examples:

Example 1

General procedure A

B29K($N^ε$[2-(2-[2-(2-[2-(Octadecandioyl-γGlu)amino]ethoxy)ethoxy]acetylamino)ethoxy]ethoxy)acetyl]), desB30 human insulin

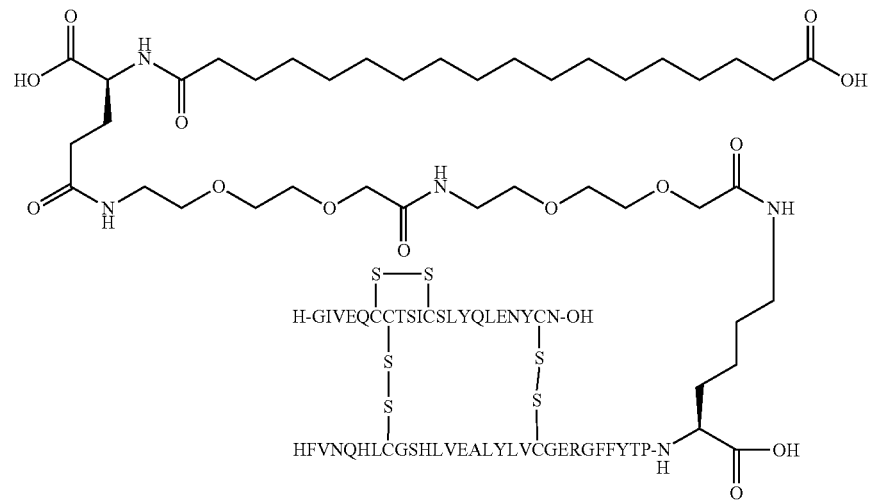

desB30 Human insulin (3.15 g, 0.55 mmol) was dissolved in 100 mM aqueous $Na_2CO_3$ (25 mL) and acetonitrile (25 mL) was added. If necessary, pH is adjusted to pH 10-10.5 by addition of 1 N NaOH. tert-Butyl octadecandioyl-Glu(OEG-OEG-OSu)-OTBU (650 mg, 0.7 mmol, preparation: See below) was dissolved in acetonitrile (10 mL) and added slowly to the insulin solution. pH was kept at 10-10.5. After 50 minutes, the reaction mixture was added water (150 mL) and pH was adjusted to 5.2 with 1N aqueous HCl. The precipitate was isolated by centrifugation and lyophilised. The crude product was added trifluoroacetic acid (TFA, 60 mL) and was left for 30 minutes at room temperature. The mixture was poured into ice cold diethyl ether (300 mL), and the precipitated product was isolated by filtration and washed twice with diethyl ether. If incomplete deprotection, the TFA treatment is repeated once. The product was purified by HPLC (acetonitrile, water, 1% TFA), followed by ion exchange chromatography (Ressource Q, 0.25%-1.25% ammonium acetate gradient in 42.5% ethanol, pH 7.5). Pure fractions were pooled, pH adjusted to 5.2 with 1 N HCl, and the precipitated material was isolated and lyophilised to afford the title insulin.

LC-MS (electrospray): m/z=1285 (M+5)/5 and 1606 (M+6)/6.

The acylation reagent for preparation of this insulin was prepared as described in the following:

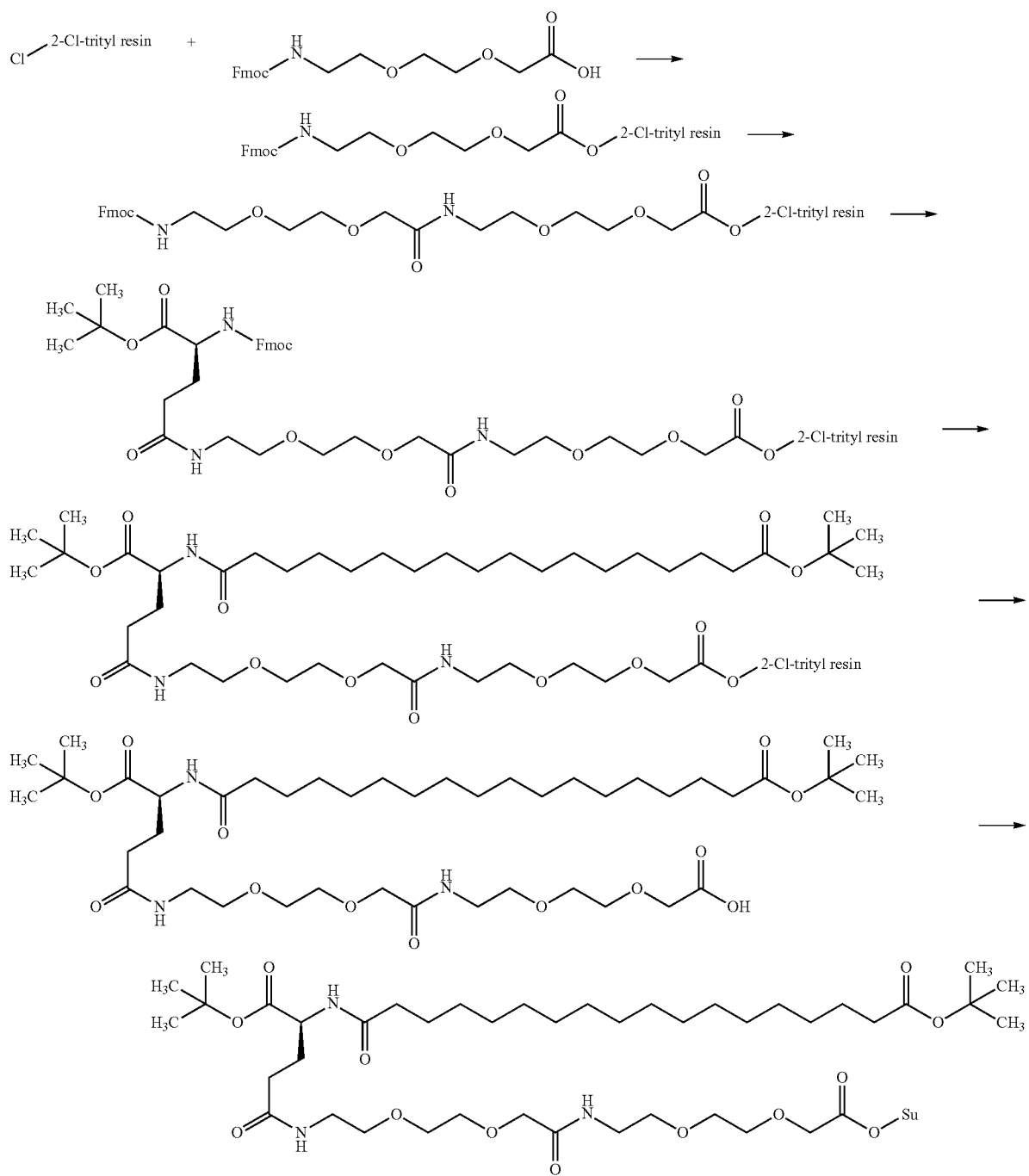

Starting resin: 2-Chlorotrityl resin, 1.60 mmol/g
1.0 g of the resin was swelled for 30 min in DCM (10 ml).
1. Acylation with Fmoc-8-Amino-3,6-Dioxaoctanoic Acid:
0.39 g (0.63 eq, 1.0 mmol) of Fmoc-8-amino-3,6-dioxaoctanoic acid (Fmoc-OEG-OH) was dissolved in DCM (15 ml) and was added to the resin. N,N-Diisopropylethylamine (DIEA) (0.44 ml, 2.5 mmol) was added dropwise. The reaction mixture was vortexed for 30 min. and then methanol (2 ml) was added and the mixture was vortexed for additional 15 min. The resin was filtered and washed with NMP (2×8 ml) and DCM (8×8 ml).
20% piperidine/NMP (8 ml) was added, standing 10 min. repeated once.
Filtered and washed with NMP (2×8 ml), DCM (3×8 ml), and NMP (5×8 ml)
A positive TNBS test gave red-coloured resins
2. Acylation with Fmoc-8-amino-3,6-dioxaoctanoic acid:
0.78 g (2 eq, 2.0 mmol) of Fmoc-8-amino-3,6-dioxaoctanoic acid was dissolved in NMP/DCM 1:1 (10 ml). 0.28 g (2.2 eq, 2.4 mmol) of HOSu was added followed by addition of 0.37 ml (2.2 eq, 2.4 mmol) of DIC. The reaction mixture was allowed to stand for 1 hour and was then added to the resin and finally 0.407 ml (2.2 eq) of DIEA was added. The mixture was vortexed for 16 hours, filtered and washed with NMP (2×8 ml), DCM (3×8 ml), and NMP (5×8 ml).
A positive TNBS test gave colourless resins.
20% piperidine/NMP (10 ml) was added, standing 10 min. repeated once.
Filtered and washed with NMP (2×8 ml), DCM (3×8 ml), and NMP (5×8 ml).
A positive TNBS test gave red-coloured resins
Acylation with Fmoc-Glu-OtBu:
0.86 g (2 eq, 2.0 mmol) of Fmoc-Glu-OtBu was dissolved in NMP/DCM 1:1 (10 ml). 0.32 g (2.2 eq, 2.4 mmol) of HOBT was added followed by addition of 0.37 ml (2.2 eq, 2.4 mmol) of DIC. The reaction mixture was allowed to stand for 20 min and was then transferred to the resin and finally 0.407 ml (2.2 eq) of DIEA was added. The mixture was vortexed for 16 hours, filtered and washed with NMP (2×8 ml), DCM (3×8 ml), and NMP (5×8 ml).
A positive TNBS test gave colourless resins.
20% piperidine/NMP (10 ml) was added, standing 10 min. repeated once.
Filtered and washed with NMP (2×8 ml), DCM (3×8 ml), and NMP (5×8 ml).
A positive TNBS test gave red-coloured resins Acylation with Octadecanedioic Acid Mono tert-Butyl Ester:
0.75 g (2 eq, 2.0 mmol) Octadecanedioic acid mono tert-butyl ester was dissolved NMP/DCM 1:1 (10 ml). 0.32 g (2.2 eq, 2.4 mmol) HOBT was added followed by addition of 0.37 ml (2.2 eq, 2.4 mmol) of DIC. The reaction mixture was allowed to stand for 20 min and was then transferred to the resin and finally 0.41 ml (2.2 eq) of DIEA was added. The mixture was vortexed for 16 hours, filtered and washed with NMP (2×8 ml), DCM (3×8 ml), and NMP (5×8 ml).
Cleavage with TFA:
8 ml of 5% TFA/DCM was added to the resin and the reaction mixture was vortexed for 2 hours, filtered and the filtrate was collected. More 5% TFA/DCM (8 ml) was added to the resin, and the mixture was vortexed for 10 min, filtered and the resin was washed with DCM (2×10 ml). The combined filtrates and washings were pH adjusted to basic using about 800 ul of DIEA. The mixture was evaporated in vacuo affording an oil (3.5 g). Diethylether (30 ml) was added and the not dissolved oil was separated by decantation and evaporated in vacuo. This afforded 1.1 g of 17-{(S)-1-tert-butoxy-carbonyl-3-[2-(2-{[2-(2-carboxymethoxyethoxy)ethylcarbamoyl]
nethoxy}ethoxy)ethylcarbamoyl]-
propylcarbamoyl}heptadecanoic acid tert-butyl ester (alternative name: Tert-butyl octadecandioyl-Glu(OEG-OEG-OH)—OTBU) as an oil.
LC-MS (Sciex100 API): m/z=846.6 (M+1)$^+$.
OSu-Activation:
The above tert-butyl octadecandioyl-Glu(OEG-OEG-OH)—OTBU (0.63 g) was dissolved in THF (35 ml). DIEA (0.255 ml, 2 eq.) was added followed by TSTU (0.45 g, 2 eq.), and the mixture was stirred at room temperature for 16 hours. The mixture was partitioned between ethyl acetate (250 ml) and aqueous NaHSO$_4$ (3×100 ml). The organic phase was dried (MgSO$_4$) and concentrated in vacuo to afford 0.65 g of 17-((S)-1-tert-butoxycarbonyl-3-{2-[2-({2-[2-(2,5-dioxopyrrolidin-1-yloxycarbonylmethoxy)-ethoxy]
ethylcarbamoyl}methoxy)ethoxy]
ethylcarbamoyl}propylcarbamoyl)heptadecanoic acid tert-butyl ester (alternative name: tert-Butyl octadecandioyl-Glu(OEG-OEG-OSu)-OTBU) as an oil.
LC-MS: m/z=943.4 (M+1)$^+$.

Example 2

General procedure A

B29K(N$^{\epsilon}$[2-(2-[2-(2-[2-(Eicosanedioyl-γGlu)amino]ethoxy)ethoxy]acetylamino)ethoxy]ethoxy)acetyl]), desB30 human insulin

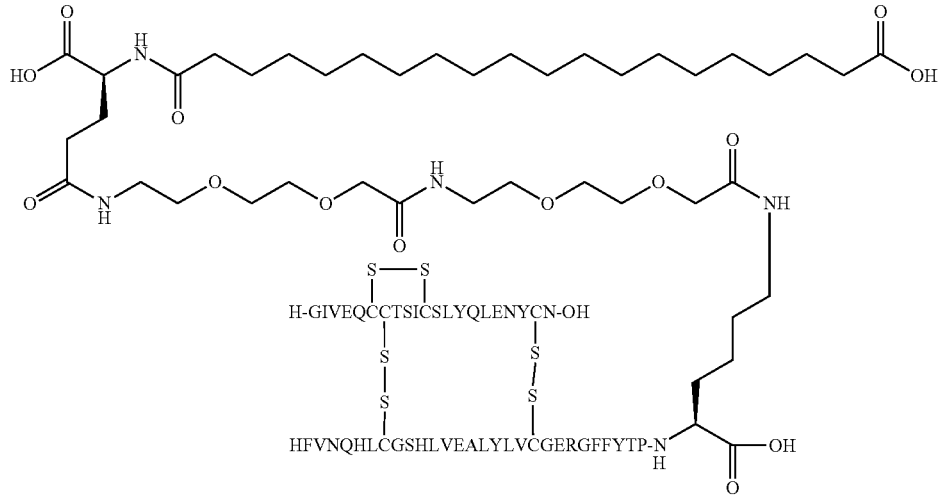

desB30 Human insulin (0.7 g) was dissolved in 100 mM aqueous Na$_2$CO$_3$ (25 mL) and acetonitrile (25 mL) was added. If necessary, pH is adjusted to pH 10-10.7 by addition of 1N NaOH. tert-Butyl eicosanedioyl-Glu(OEG-OEG-OSu)-OTBU (140 mg, prepared similarly as described above using eicisanedioic acid mono tert-butyl ester instead of octadecanedioic acid mono tert-butyl ester) was dissolved in acetonitrile (3 mL) and added slowly to the insulin solution. pH was kept at 10.5. After 45 minutes, the reaction mixture was added water (150 mL) and pH was adjusted to 5.2 with 1N aqueous HCl. The precipitate was isolated by centrifugation and lyophilised. The crude product was added trifluoroacetic acid (TFA, 7 mL) and water (0.35 mL) and was left for 50 minutes at room temperature. The mixture was added dichloromethane (20 mL) and concentrated in vacuo. The residue was stripped twice with dichloromethane. The product was purified by HPLC (acetonitrile, water, 1% TFA). Pure fractions were pooled and lyophilised to afford the title insulin.

MALDI-TOF MS: m/z=6449.

Example 3

General procedure A

B28D, B29K(N$^\epsilon$-[2-(2-[2-(2-[2-(Octadecandioyl-γGlu)amino]ethoxy)ethoxy]acetylamino)ethoxy]-ethoxy)acetyl]) human insulin

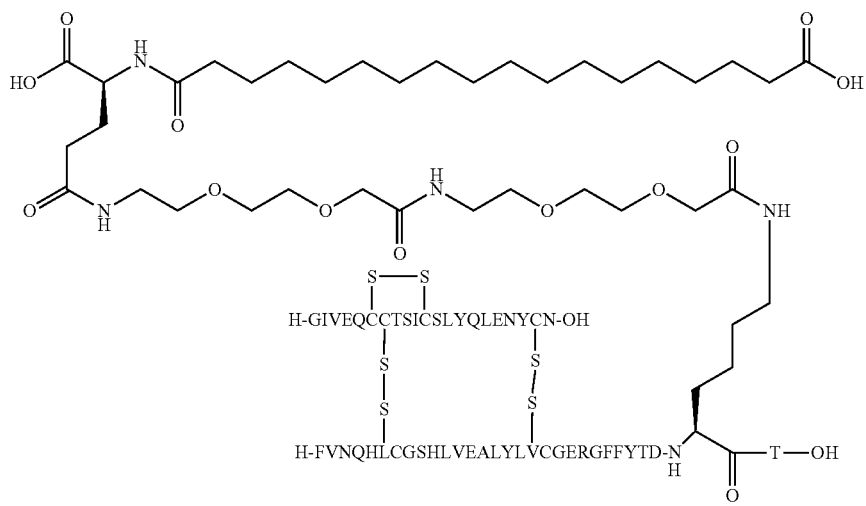

LC-MS (electrospray): m/z: 1635.9 (M+4)/4

Example 4

General procedure A

B29K(N$^\epsilon$-[2-(2-{2-[2-(2-{2-[2-(2-(Octadecandioyl-γGlu)aminoethoxy)ethoxy]acetylamino}ethoxy)ethoxy]-acetylamino}ethoxy)ethoxy]acetyl), desB30 human insulin

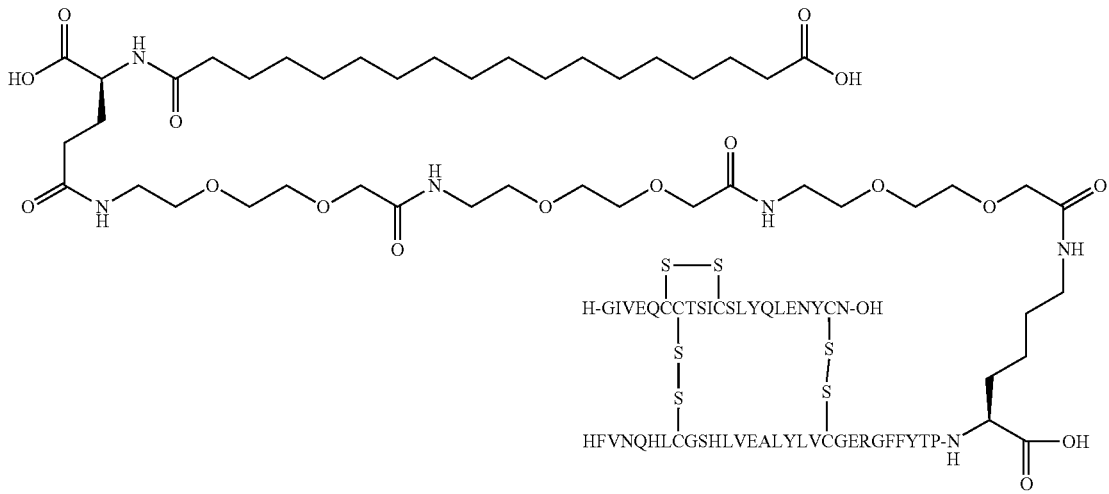

LC-MS (electrospray): m/z: 1642 (M+4)/4

Example 5
General Procedure A
B29K(Nᵉ-[2-(2-{2-[2-(2-{2-[2-(2-{2-[2-(2-(Octadecandioyl-γGlu)aminoethoxy)ethoxy]acetylamino}-ethoxy)ethoxy]acetylamino}ethoxy)ethoxy]acetylamino}ethoxy)ethoxy]acetyl) human insulin
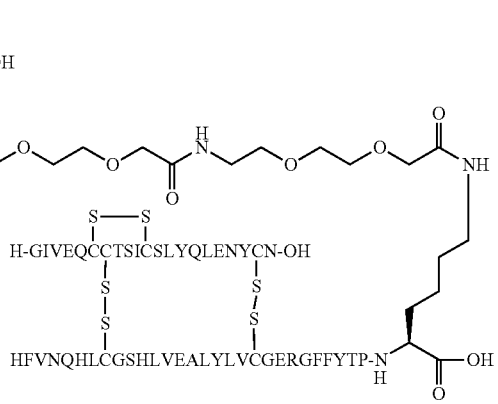
MALDI-TOF MS: 6711
Example 6
General Procedure A
B29K(Nᵉ-{2-[2-(2-{2-[2-(Octadendioylamino)ethoxy]ethoxy}acetylamino)ethoxy]ethoxy}acetyl-gGlu), desB30 human insulin
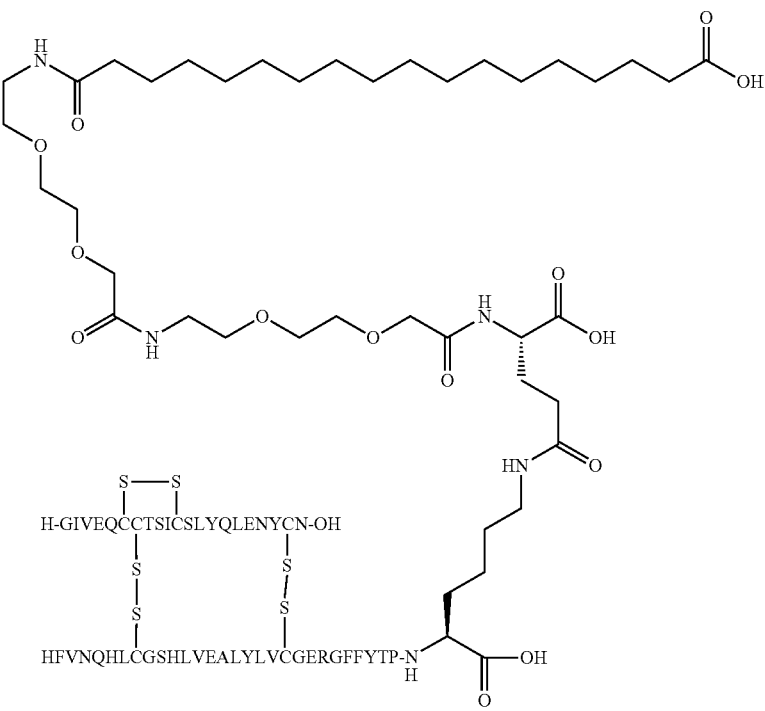
MALDI-TOF MS: 6428

Example 7
General Procedure A
B29K(Nᵉ[2-(2-[2-(2-[2-(4-[(Octadecandioylamino)methyl]-trans-cyclohexanecarboxyl)amino]ethoxy)ethoxy]acetylamino)ethoxy]ethoxy)acetyl]), desB30 human insulin
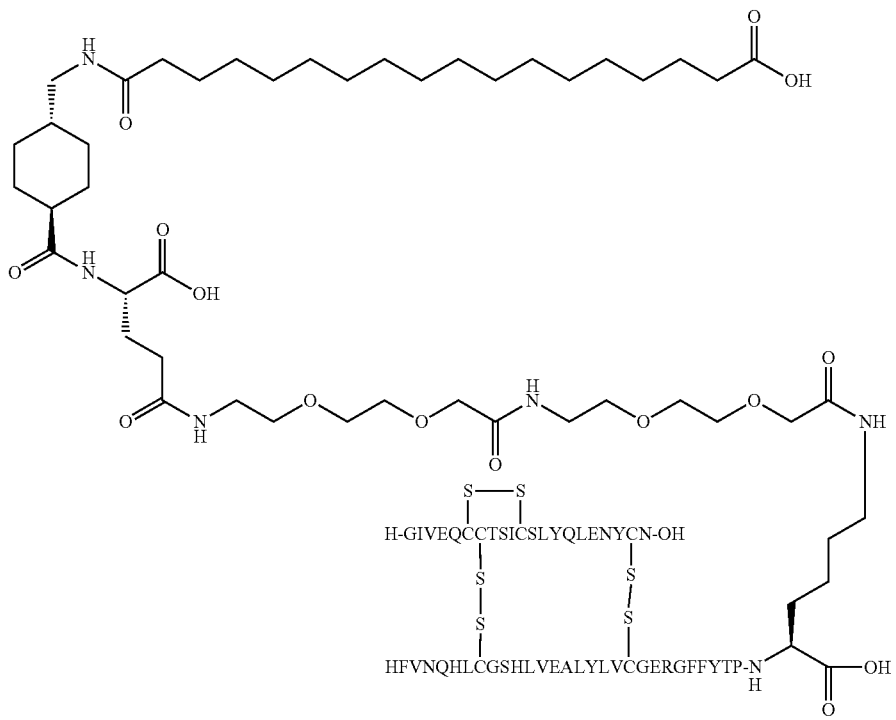
MALDI-TOF MS: 6563

Example 8
General Procedure A
B29K(N^ε[2-(2-[2-(2-[2-(4-[(Eicosanedioylamino)methyl]-trans-cyclohexanecarboxyl)amino]ethoxy)-ethoxy]acetylamino)ethoxy]ethoxy)acetyl]), desB30 human insulin
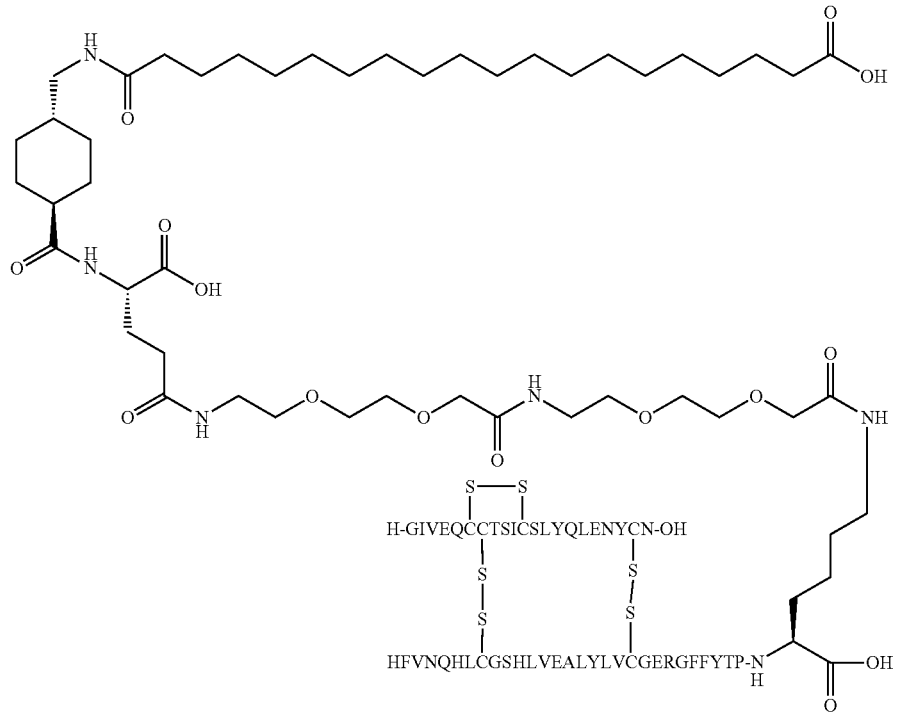
MALDI-TOF MS: 6594
Example 9
General Procedure A
B29K(N(eps)-[2-(2-[2-(2-[2-(Heptadecandioyl-gGlu)amino]ethoxy)ethoxy]acetylamino)ethoxy]ethoxy)-acetyl]), desB30 human insulin
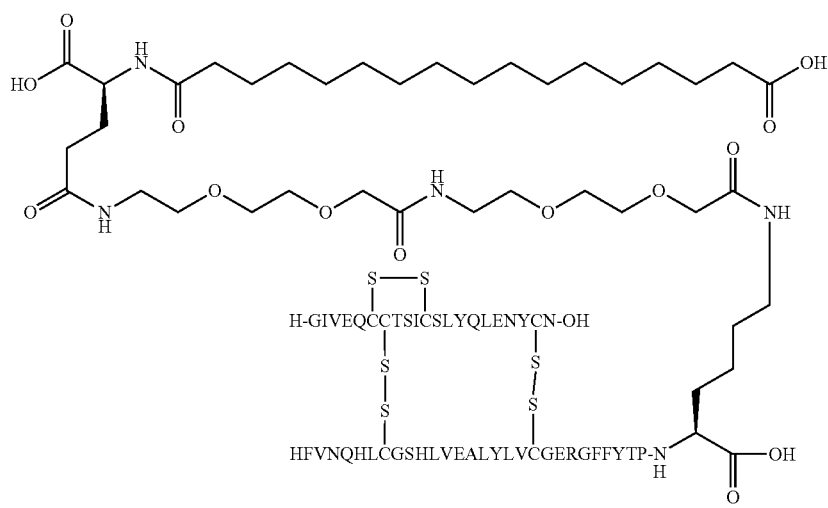
LC-MS (electrospray): m/z: 1603 (M+4)/4

Example 10

General Procedure A

B29K(N(eps)-[2-(2-[2-(2-[2-(Hexadecandioyl-gGlu)amino]ethoxy)ethoxy]acetylamino)ethoxy]ethoxy)acetyl]), desB30 human insulin

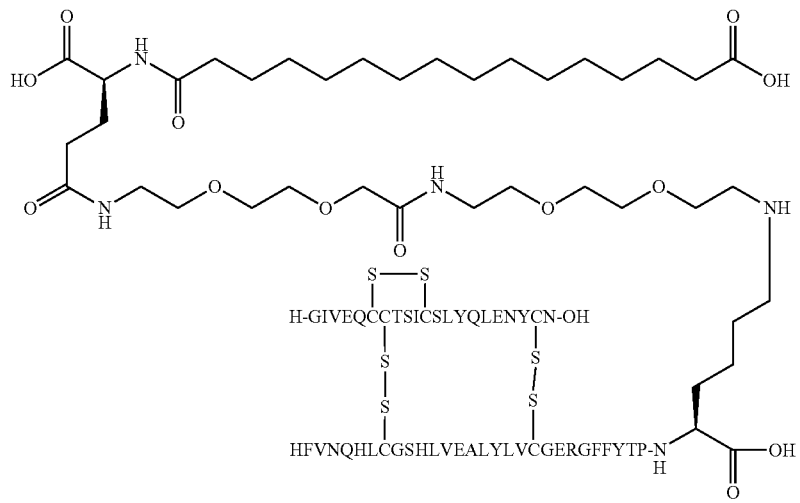

MALDI-TOF MS: 6395

Example 11

Insulin Receptor Binding of the Insulin Derivatives of this Invention

The affinity of the insulin derivatives of this invention for the human insulin receptor is determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 ml of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl reagent mix is then added to each well in the Packard Optiplate and a dilution series of the insulin derivative is made in the Optiplate from appropriate samples. The samples are then incubated for 16 hours while gently shaken. The phases are the then separated by centrifugation for 1 min and the plates counted in a Topcounter. The binding data were fitted using the nonlinear regression algorithm in the GraphPad Prism 2.01 (GraphPad Software, San Diego, Calif.).

The binding buffer was also modified to possess 4.5% HSA (human serum albumin) in order to better simulate or "mimic" the physiological situation of receptor binding.

Insulin Receptor (A-isoform) binding data of selected compounds of the invention:

| Ex # | Modification | Parent Insulin | IR-A affinity 0% HSA (% relative to human insulin) | IR-A affinity 4.5% HSA (% relative to human insulin) |
|---|---|---|---|---|
|  | C18-gGlu | desB30 | 9.2 | 0.16 |
| 1 | C18-gGlu-OEG-OEG | desB30 | 12.6 | 1.35 |
| 2 | C20-gGlu-OEG-OEG | desB30 | 8.6 | 1.96 |
| 3 | C18-gGlu-OEG-OEG | B28D | 4.7 | ND |
| 4 | C18-gGlu-(OEG)$_3$ | desB30 | 10.0 | ND |
| 5 | C18-gGlu-(OEG)$_4$ | desB30 | 8.9 | ND |
| 6 | C18-OEG-OEG-gGlu | desB30 | 11.4 | ND |
| 7 | C18-Trx-gGlu-(OEG)$_2$ | desB30 | 10.1 | ND |
| 8 | C20-Trx-gGlu-(OEG)$_2$ | desB30 | 6.7 | ND |
| 9 | C17-gGlu-OEG-OEG | desB30 | 10.8 | ND |
| 10 | C16-gGlu-OEG-OEG | desB30 | 34.7 | 1.18 |

The "modifications" in the table above have been included for the sake of easier reading. The complete structure/sequence of these insulins can be found in the examples.

As can be seen from the table, inclusion of repeating units of alkylene glycol containing amino acids in the side chain as it is done in the compounds of this invention improves the insulin receptor affinity in presence of 4.5% HSA ten-fold.

Example 12

Blood Glucose Lowering Effect after i.v. Bolus Injection in Rat of the Insulin Derivatives of this Invention Male Wistar rats, 200-300 g, fasted for 18 h, is anesthetized using either Hypnorm-Dormicum s.c. (1.25 mg/ml Dormicum, 2.5 mg/ml fluanisone, 0.079 mg/ml fentanyl citrate) 2 ml/kg as a priming dose (to timepoint −30 min prior to test substance dosing) and additional 1 ml/kg every 20 minutes.

The animals are dosed with an intravenous injection (tail vein), 1 ml/kg, of control and test compounds (usual dose range 0.125-20 nmol/kg). Blood samples for the determination of whole blood glucose concentration are collected in heparinized 10 µl glass tubes by puncture of the capillary vessels in the tail tip to time −20 min and 0 min (before dosing), and to time 10, 20, 30, 40, 60, 80, 120, and 180 min after dosing. Blood glucose concentrations are measured after dilution in analysis buffer by the immobilized glucose oxidase method using an EBIO Plus autoanalyzer (Eppendorf, Germany). Mean plasma glucose concentrations courses (mean±SEM) are made for each dose and each compound.

Example 13

Potency of the Insulin Derivatives of this Invention Relative to Human Insulin

Sprague Dawley male rats weighing 238-383 g on the experimental day are used for the clamp experiment. The rats have free access to feed under controlled ambient conditions and are fasted over-night (from 3 pm) prior to the clamp experiment.
Experimental Protocol:

The rats are acclimatized in the animal facilities for at least 1 week prior to the surgical procedure. Approximately 1 week prior to the clamp experiment, Tygon catheters are inserted under halothane anaesthesia into the jugular vein (for infusion) and the carotid artery (for blood sampling) and exteriorised and fixed on the back of the neck. The rats are given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) is administered during anaesthesia and Rimadyl (1.5 mg/kg, s.c.) is administered after full recovery from the anaesthesia (2-3 h) and again once daily for 2 days.

At 7 am on the experimental day, overnight fasted (from 3 pm the previous day) rats are weighed and connected to the sampling syringes and infusion system (Harvard 22 Basic pumps, Harvard, and Perfectum Hypodermic glass syringe, Aldrich) and then placed into individual clamp cages where they rest for ca. 45 min before start of experiment. The rats are able to move freely on their usual bedding during the entire experiment and have free access to drinking water. After a 30 min basal period during which plasma glucose levels were measured at 10 min intervals, the insulin derivative to be tested and human insulin (one dose level per rat, n=6-7 per dose level) are infused (i.v.) at a constant rate for 300 min. Plasma glucose levels are measured at 10 min intervals throughout and infusion of 20% aqueous glucose is adjusted accordingly in order to maintain euglyceamia. Samples of re-suspended erythrocytes are pooled from each rat and returned in about ½ ml volumes via the carotid catheter.

On each experimental day, samples of the solutions of the individual insulin derivatives to be tested and the human insulin solution are taken before and at the end of the clamp experiments and the concentrations of the peptides are confirmed by HPLC. Plasma concentrations of rat insulin and C-peptide as well as of the insulin derivative to be tested and human insulin are measured at relevant time points before and at the end of the studies. Rats are killed at the end of experiment using a pentobarbital overdose.

All compounds according to the present invention tested showed a significantly higher potency than the potency of a known compound, i.e., B29K($N_\epsilon$-octadecandioyl-γGlu), desB30 human insulin, given as steady-state iv infusion clamp potency. Hence, the compounds of this invention have an improved potency.

Example 14

Pulmonary Delivery of Insulin Derivatives to Rats

The test substance will be dosed pulmonary by the drop instillation method. In brief, male Wistar rats (app.250 g) are anaesthesized in app. 60 ml fentanyl/dehydrodenzperidol/dormicum given as a 6.6 ml/kg sc primingdose and followed by 3 maintainance doses of 3.3 ml/kg sc with an interval of 30 min. Ten minutes after the induction of anaesthesia, basal samples are obtained from the tail vein (t=−20 min) followed by a basal sample immediately prior to the dosing of test substance (t=0). At t=0, the test substance is dosed intra tracheally into one lung. A special cannula with rounded ending is mounted on a syringe containing the 200 ul air and test substance (1 ml/kg). Via the orifice, the cannula is introduced into the trachea and is forwarded into one of the main bronchi—just passing the bifurcature. During the insertion, the neck is palpated from the exterior to assure intratracheal positioning. The content of the syringe is injected followed by 2 sec pause. Thereafter, the cannula is slowly drawn back. The rats are kept anaesthesized during the test (blood samples for up to 4 or 8 hrs) and are euthanized after the experiment.

SEQUENCE LISTINGS

SEQ ID NO:1 is the A1-A21 chain of examples 1-10. SEQ ID NO:2 is the B1-B28 chain of example 1, 2 and 4-10. SEQ ID NO:3 is the B1-B28 chain of example 3.

FIGURE

FIG. 1 gives the result from a rat intratracheal drop instillation of the insulin of example 1.

---

What is claimed is:

1. An acylated human insulin, wherein an acyl moiety is attached to the epsilon amino group of B29K of the parent insulin and wherein said acyl moiety comprises repeating units of alkylene glycol containing amino acids and wherein there is only one lysine residue in the parent insulin, wherein the acyl moiety is a group of formula (I):

$$\text{Acy-AA1}_n\text{-AA2}_m\text{-AA3}_p\text{-} \qquad (I),$$

wherein
  n is an integer in the range 1-3,
  m is 0 or an integer in the range 1-6,
  p is an integer in the range 2-30
Acy is a fatty acid or a fatty diacid comprising 8 to 24 carbon atoms from which a hydroxy group has been removed from the fatty acid and a hydroxy group has been removed from one of the carboxy groups in the fatty diacid,
AA1 is a neutral cyclic amino acid from which a hydroxy group has been removed from the carboxy group and a hydrogen atom has been removed from the amino group, wherein AA1 is selected from

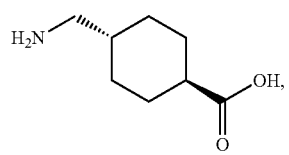

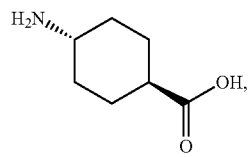

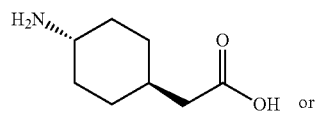 or

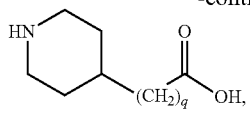

wherein q is 0, 1, 2, 3 or 4,

AA2 is an acidic amino acid from which a hydroxy group has been removed from the carboxy group and a hydrogen atom has been removed from the amino group, AA3 is a neutral, alkyleneglycol-containing amino acid from which a hydroxy group has been removed from the carboxy group and a hydrogen atom has been removed from the amino group, the order in which AA1, AA2 and AA3 appears in the group of formula I can be interchanged independently, and the connections between Acy, AA1, AA2 and/or AA3 are amide bonds.

2. An acylated insulin, according to claim 1, wherein AA1 is

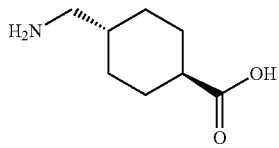 [SMILES: NC[C@H]1CC[C@H](C(=O)O)CC1]

from which a hydroxy group has been removed from the carboxy group and a hydrogen atom has been removed from the amino group.

3. An acylated insulin, according to claim 2, wherein AA2 is Glu (α or γ, L or D), Asp (α or β, L or D),

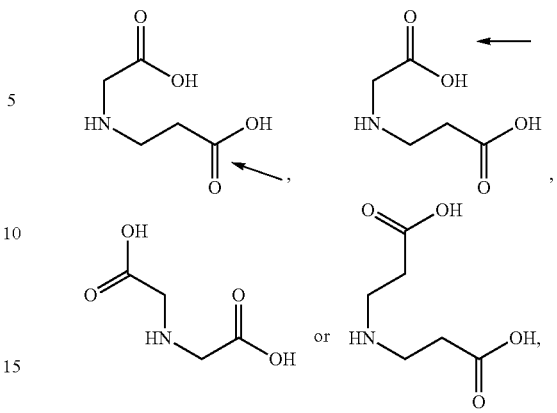

from which a hydroxy group has been removed from the carboxy group and a hydrogen atom has been removed from the amino group, and wherein the arrows indicate the attachment point to the amino group of AA3.

4. An acylated insulin according to claim 1, which is selected from the group consisting of B29K(N$^\epsilon$[2-(2-[2-(2-[2-(4-[(octadecandioylamino)methyl]-trans-cyclohexanecarboxyl)amino]-ethoxy) ethoxy]acetylamino)ethoxy]ethoxy)acetyl], desB30 human insulin; and B29K(N$^\epsilon$[2-(2-[2-(2-[2-(4-[(eicosanedioylamino)methyl]-trans-cyclohexanecarboxyl)amino]-ethoxy) ethoxy]acetylamino)ethoxy]ethoxy)acetyl]), desB30 human insulin.

* * * * *

SEQUENCE LISTING

<160> NUMBER OF SEQ ID NOS: 3

<210> SEQ ID NO 1
<211> LENGTH: 21
<212> TYPE: PRT
<213> ORGANISM: Artificial Sequence
<220> FEATURE:
<223> OTHER INFORMATION: Synthetic

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 28
<212> TYPE: PRT
<213> ORGANISM: Artificial Sequence
<220> FEATURE:
<223> OTHER INFORMATION: Synthetic

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro
            20                  25

<210> SEQ ID NO 3
<211> LENGTH: 28
<212> TYPE: PRT
<213> ORGANISM: Artificial Sequence
<220> FEATURE:
<223> OTHER INFORMATION: Synthetic

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp
            20                  25